United States Patent
Liniger et al.

(10) Patent No.: US 7,850,652 B2
(45) Date of Patent: Dec. 14, 2010

(54) INSERTION HEAD FOR MEDICAL OR PHARMACEUTICAL APPLICATIONS

(75) Inventors: Jurg Liniger, Ostermundigen (CH); Martin Wyss, Burgdorf (CH); Christian Thalmann, Hostettli (CH); Michael Weibel, Alchenfluh (CH)

(73) Assignee: Roche Diagnostics International AG, Steinhausen (CH)

( * ) Notice: Subject to any disclaimer, the term of this patent is extended or adjusted under 35 U.S.C. 154(b) by 143 days.

(21) Appl. No.: 12/047,666

(22) Filed: Mar. 13, 2008

(65) Prior Publication Data

US 2008/0228144 A1  Sep. 18, 2008

(30) Foreign Application Priority Data

Mar. 14, 2007 (EP) ................... 07005217

(51) Int. Cl.
*A61M 5/178* (2006.01)

(52) U.S. Cl. .............. 604/164.08; 604/164.01; 604/263; 604/174

(58) Field of Classification Search ........... 604/164.01, 604/263, 174, 177, 192, 198, 164.08
See application file for complete search history.

(56) References Cited

U.S. PATENT DOCUMENTS

| | | |
|---|---|---|
| 4,306,563 A | 12/1981 | Iwatschenko |
| 4,631,058 A | 12/1986 | Raines |
| 4,755,173 A | 7/1988 | Konopka et al. |
| 4,835,248 A | 5/1989 | Bader et al. |
| 4,863,432 A | 9/1989 | Kvalo |
| 4,927,603 A | 5/1990 | Fischer et al. |
| 4,968,303 A | 11/1990 | Clarke et al. |
| 5,176,662 A | 1/1993 | Bartholomew et al. |
| 5,522,803 A | 6/1996 | Teissen-Simony |
| 5,545,143 A | 8/1996 | Fischell |
| 5,584,813 A | 12/1996 | Livingston et al. |
| 5,637,094 A | 6/1997 | Stewart, Jr. et al. |

(Continued)

FOREIGN PATENT DOCUMENTS

DE  19821723 C1  11/1999

(Continued)

OTHER PUBLICATIONS

European Search Report for 07005215.

(Continued)

*Primary Examiner*—Nicholas D Lucchesi
*Assistant Examiner*—Brooke M Matney
(74) *Attorney, Agent, or Firm*—Dinsmore & Shohl LLP

(57) ABSTRACT

An insertion head for medical use, including a housing formed by two housing parts, a puncture needle and a flexible cannula supported by the puncture needle, wherein before use the puncture needle and cannula are arranged in a protected position inside the housing and can be deployed by gripping the housing parts and moving at least one of the parts relative to the other, wherein upon deployment the puncture needle and cannula can be inserted into the body of a patient, and wherein after insertion the puncture needle can be removed from the cannula by moving the housing and puncture needle away from the body counter to the direction of insertion, the puncture needle being automatically pivoted into a protected position in the housing.

29 Claims, 22 Drawing Sheets

U.S. PATENT DOCUMENTS

| | | | |
|---|---|---|---|
| 5,814,020 A | 9/1998 | Gross | |
| 5,848,990 A | 12/1998 | Cirelli et al. | |
| 5,858,001 A | 1/1999 | Tsals et al. | |
| 5,951,522 A | 9/1999 | Rosato et al. | |
| 5,957,895 A | 9/1999 | Sage et al. | |
| 5,968,011 A | 10/1999 | Larsen et al. | |
| 5,980,506 A | 11/1999 | Mathiasen | |
| 5,997,504 A | 12/1999 | Bell | |
| 6,017,328 A | 1/2000 | Fischell et al. | |
| 6,056,718 A | 5/2000 | Funderburk et al. | |
| 6,090,068 A | 7/2000 | Chanut | |
| 6,261,259 B1 | 7/2001 | Bell | |
| 6,302,866 B1 | 10/2001 | Marggi | |
| 6,355,021 B1 | 3/2002 | Nielsen et al. | |
| 6,379,335 B1 | 4/2002 | Rigon et al. | |
| 6,419,699 B1 | 7/2002 | Schuessler | |
| 6,500,150 B1 | 12/2002 | Gross et al. | |
| 6,520,938 B1 | 2/2003 | Funderburk et al. | |
| 6,537,255 B1 | 3/2003 | Raines | |
| 6,579,267 B2 | 6/2003 | Lynch et al. | |
| 6,607,509 B2 | 8/2003 | Bobroff et al. | |
| 6,676,633 B2 | 1/2004 | Smith et al. | |
| 6,749,588 B1 | 6/2004 | Howell et al. | |
| 6,749,589 B1 | 6/2004 | Douglas et al. | |
| 6,755,805 B1 | 6/2004 | Reid | |
| 6,824,530 B2 | 11/2004 | Wagner et al. | |
| 6,840,922 B2 | 1/2005 | Nielsen et al. | |
| 6,878,134 B2 | 4/2005 | Rogers et al. | |
| 6,887,270 B2 | 5/2005 | Miller et al. | |
| 6,911,020 B2 | 6/2005 | Raines | |
| 6,921,388 B2 | 7/2005 | Swenson | |
| 6,923,791 B2 | 8/2005 | Douglas | |
| 6,949,084 B2 | 9/2005 | Marggi et al. | |
| 6,969,372 B1 | 11/2005 | Halseth | |
| 6,997,902 B2 | 2/2006 | Thorne et al. | |
| D526,409 S | 8/2006 | Nielsen et al. | |
| 7,097,637 B2 | 8/2006 | Triplett et al. | |
| 7,147,623 B2 | 12/2006 | Mathiasen | |
| 7,214,207 B2 | 5/2007 | Lynch et al. | |
| 2002/0045867 A1 | 4/2002 | Nielsen et al. | |
| 2002/0123724 A1 | 9/2002 | Douglas et al. | |
| 2002/0193744 A1 | 12/2002 | Alesi et al. | |
| 2003/0069546 A1 | 4/2003 | Sandstrom et al. | |
| 2003/0083624 A1 | 5/2003 | Smith et al. | |
| 2003/0105449 A1 | 6/2003 | Raines | |
| 2003/0125669 A1 | 7/2003 | Safabash et al. | |
| 2003/0181874 A1 | 9/2003 | Bressler et al. | |
| 2003/0199823 A1 | 10/2003 | Bobroff et al. | |
| 2004/0044306 A1 | 3/2004 | Lynch et al. | |
| 2004/0158207 A1* | 8/2004 | Hunn et al. | 604/164.01 |
| 2004/0158230 A1 | 8/2004 | Hunn et al. | |
| 2004/0215154 A1 | 10/2004 | Hwang et al. | |
| 2005/0035014 A1 | 2/2005 | Cane | |
| 2005/0283125 A1 | 12/2005 | Barkhahn et al. | |
| 2006/0015063 A1 | 1/2006 | Butikofer et al. | |
| 2006/0030824 A1 | 2/2006 | Hunn et al. | |
| 2006/0173414 A1 | 8/2006 | Buetikofer et al. | |
| 2006/0183985 A1 | 8/2006 | Brister et al. | |
| 2006/0229573 A1 | 10/2006 | Lamborne | |
| 2007/0016149 A1 | 1/2007 | Hunn et al. | |
| 2007/0129688 A1 | 6/2007 | Scheurer et al. | |

FOREIGN PATENT DOCUMENTS

| | | | |
|---|---|---|---|
| DE | 10117286 A1 | 10/2002 | |
| DE | 20320207 U1 | 11/2004 | |
| DE | 202004017862 U1 | 2/2005 | |
| DE | 102004002472 A1 | 8/2005 | |
| DE | 102004039408 A1 | 3/2006 | |
| EP | 1652547 A1 | 5/2006 | |
| EP | 1764125 A1 | 3/2007 | |
| FR | 2725902 A1 | 4/1996 | |
| FR | 2752164 A1 * | 2/1998 | |
| WO | 02081012 A2 | 10/2002 | |
| WO | 2004029457 A1 | 4/2004 | |
| WO | 2004064593 A2 | 8/2004 | |
| WO | 2004064898 A1 | 8/2004 | |
| WO | 2004098682 A2 | 11/2004 | |
| WO | 2004101071 A1 | 11/2004 | |
| WO | 2004110527 A1 | 12/2004 | |
| WO | 2005037184 A2 | 4/2005 | |
| WO | 2005065748 A1 | 7/2005 | |
| WO | 2006015507 A2 | 2/2006 | |
| WO | 2006108185 A1 | 10/2006 | |
| WO | 2006129196 A1 | 12/2006 | |

OTHER PUBLICATIONS

European Search Report for 07005216.
European Search Report for 07005217.
US Office Action dated Dec. 10, 2009 pertaining to U.S. Appl. No. 12/047,643.
US Notice of Allowance dated Jun. 7, 2010 pertaining to U.S. Appl. No. 11/673,939.
US Office Action dated Mar. 24, 2010 pertaining to U.S. Appl. No. 11/673,939.
US Office Action dated Dec. 29, 2009 pertaining to U.S. Appl. No. 11/673,939.
US Office Action dated May 27, 2009 pertaining to U.S. Appl. No. 11/673,939.
US Office Action dated Jul. 11, 2008 pertaining to U.S. Appl. No. 11/673,939.
US Office Action dated Nov. 28, 2007 pertaining to U.S. Appl. No. 11/673,939.
US Office Action dated Jun. 14, 2007 pertaining to U.S. Appl. No. 11/673,939.
US Notice of Allowance dated Apr. 2, 2010 pertaining to U.S. Appl. No. 12/047,551.
US Office Action dated Dec. 23, 2009 pertaining to U.S. Appl. No. 12/047,551.
US Office Action dated Sep. 17, 2009 pertaining to U.S. Appl. No. 12/047,551.
Notice of Allowance dated Jul. 8, 2010 pertaining to U.S. Appl. No. 12/047,643.

* cited by examiner

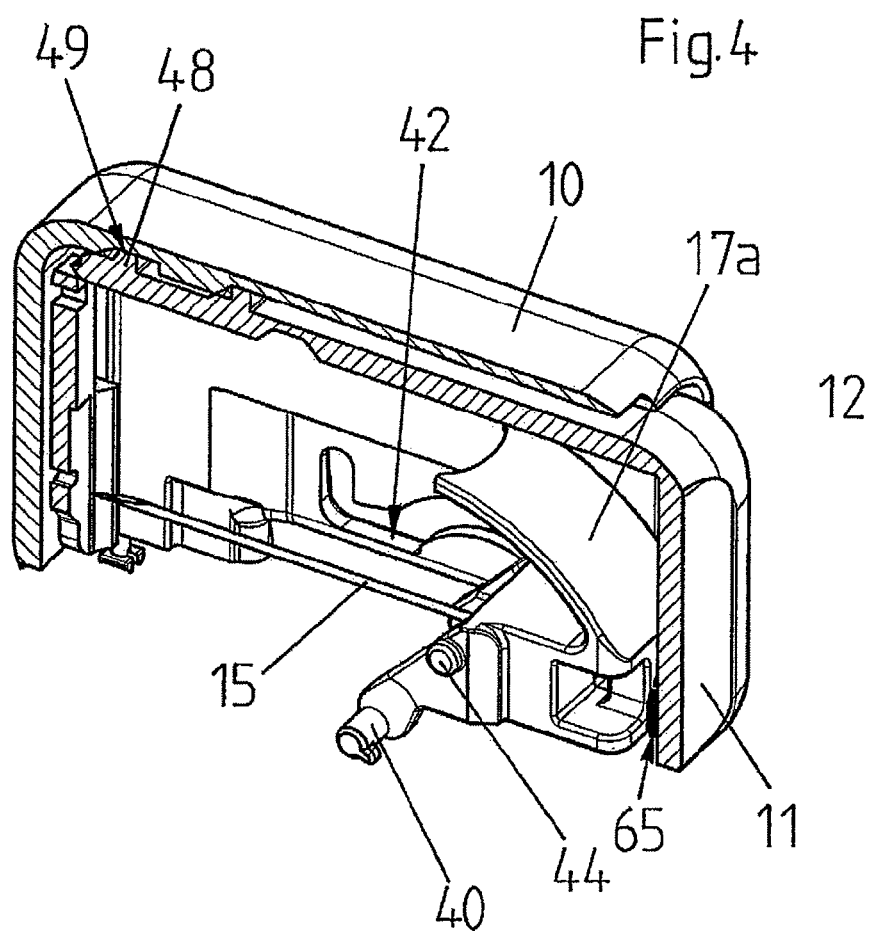

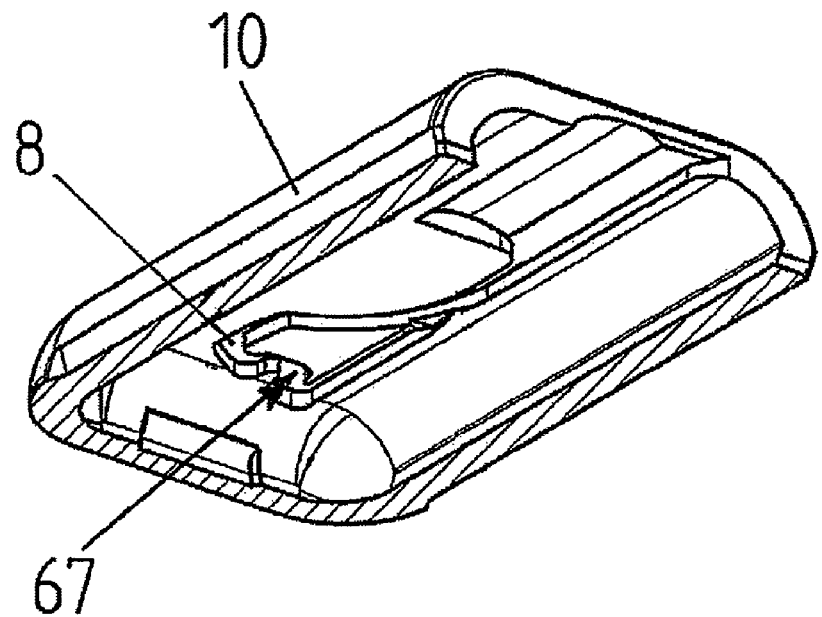
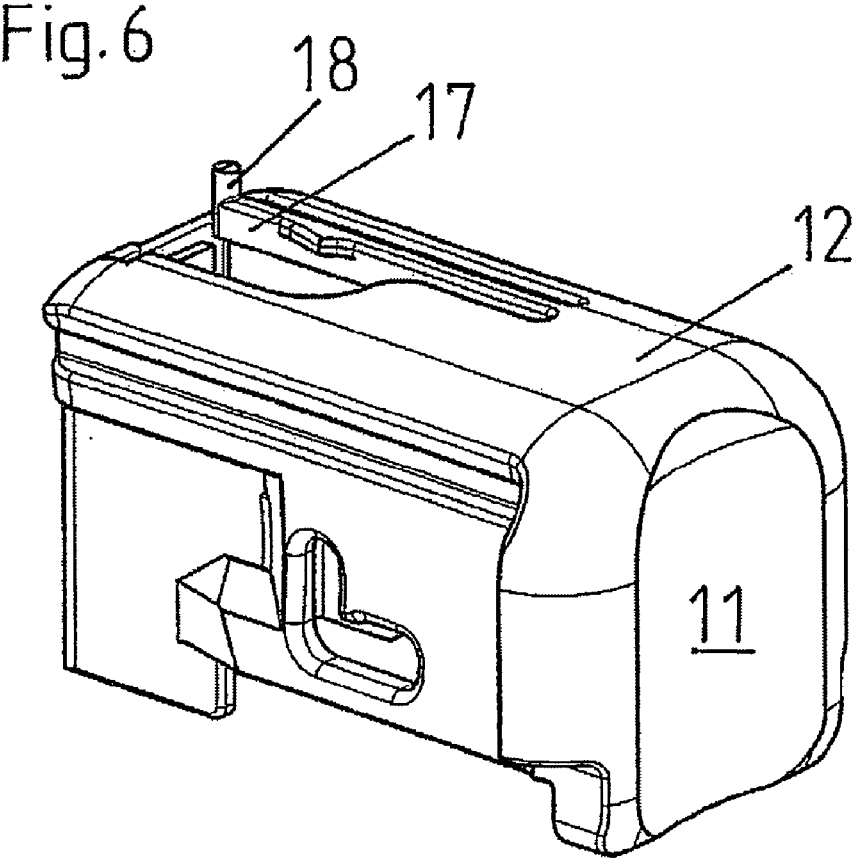

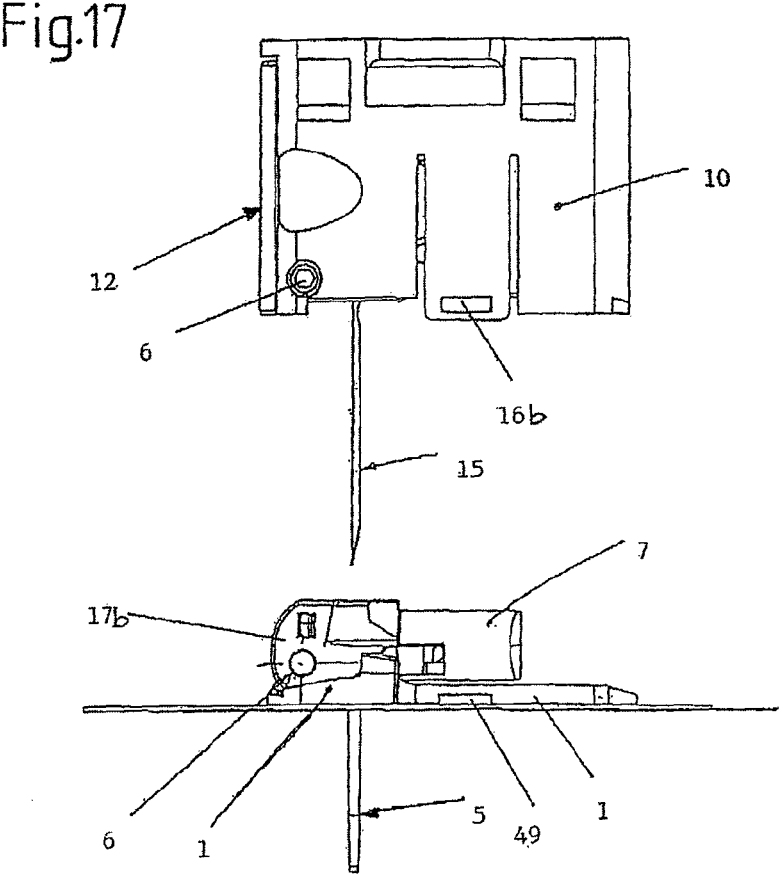
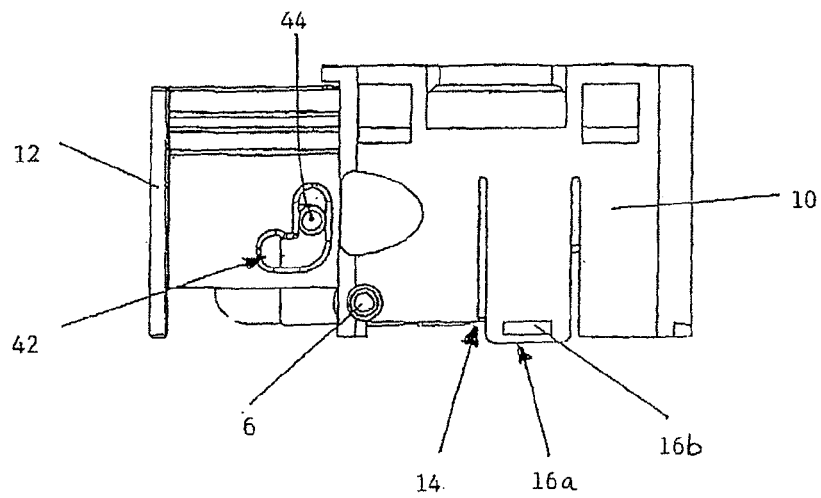

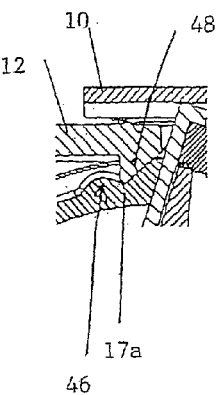
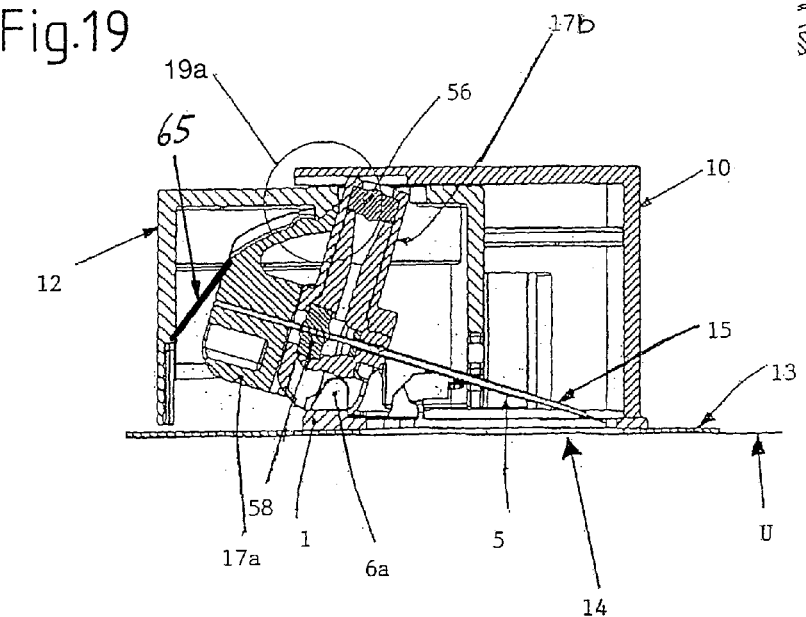
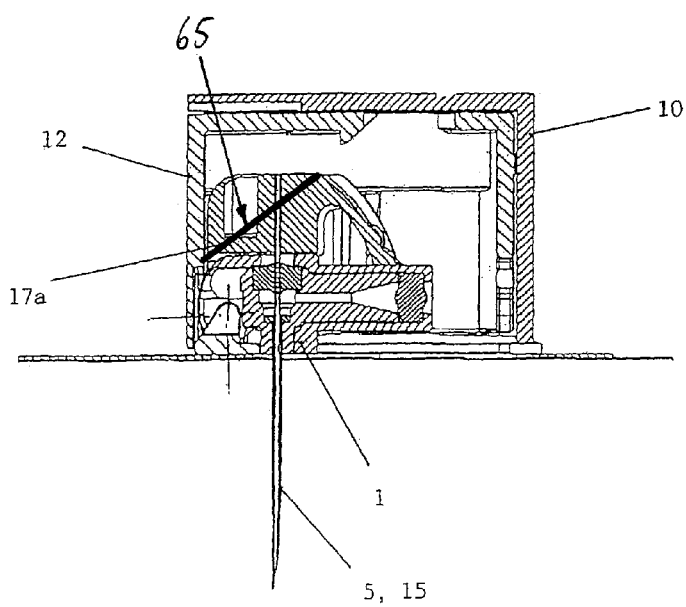

INSERTION HEAD FOR MEDICAL OR PHARMACEUTICAL APPLICATIONS

CROSS REFERENCE TO RELATED APPLICATIONS

This application claims priority to European Application No. 07005217.0, filed on Mar. 14, 2007, the contents of which are hereby incorporated in their entirety by reference herein.

BACKGROUND

The present invention relates to devices for infusing, injecting, administering, delivering or dispensing substances, and to methods of making and using such devices. More particularly, it relates to an insertion head for medical or pharmaceutical applications or uses, which insertion head can be placed on organic tissue, e.g. human skin, and has an insertion device that penetrates into the tissue when the insertion head is placed on the tissue or, if appropriate, after the insertion head has been placed on the tissue. In some embodiments of the present present invention, the insertion head may be a component of an infusion set for administering a medicament.

DE 198 21 723 C1 discloses an insertion head that comprises a base, a flexible cannula and a puncture needle. The cannula protrudes from an underside of the base. The puncture needle stabilizes the cannula while the cannula is inserted into the tissue of a patient. For this stabilizing, the puncture needle extends through the cannula, and the cannula snugly encloses the puncture needle. To provide protection against stick injuries, a needle guard is secured releasably on the base. The puncture needle enclosed by the cannula and protruding downwards from the underside of the insertion head, and in particular also the needle guard, greatly increase the volume of the insertion head and therefore also that of its packaging. Moreover, the removal of the needle guard is awkward and is associated with a risk of injury.

German patent application No. 10 2004 039 408.3 relates to an insertion head comprising a base, with an underside that can be placed on organic tissue, and a space-saving insertion device that is mounted movably from the base and can be inserted into the tissue. During storage, transport and handling, and until insertion into the tissue, the insertion device assumes a protected position. For insertion, it can be moved out of the protected position into an insertion position. The preferred type of movement disclosed is a pivoting movement. To be able to effect the movement of the insertion device, a grip is provided for the user, which grip can be pivoted jointly with the insertion device. The insertion head is advantageously compact and, moreover, does not require the removal of a needle guard. To move the insertion device into the insertion position, however, the user has to grip the insertion head with one hand and use the other hand to pivot the grip along with the insertion device.

SUMMARY

It is an object of the present invention to make available an insertion head which has an integrated protection for an insertion device, for example comparable to the insertion head of German patent application No. 10 2004 039 408.3, but which is easier to use and can be used and/or maneuvered using just one hand.

In one embodiment, the present invention comprises an insertion head for medical use, including a housing formed by two housing parts, a puncture needle and a flexible cannula supported by the puncture needle, wherein before use the puncture needle and cannula are in a protected position inside the housing and can be deployed by gripping the housing parts and moving at least one of the parts relative to the other, wherein upon deployment the puncture needle and cannula can be inserted into the body of a patient, and wherein after insertion the puncture needle can be removed from the cannula by moving the housing and puncture needle away from the body counter to the direction of insertion, the puncture needle being automatically pivoted into a protected position in the housing.

In one embodiment, the present invention comprises an insertion head for medical applications, with a flexible cannula supported by a puncture needle. In the state in which the insertion head is offered for sale, the puncture needle and cannula are arranged in a protected position inside two slideable housing halves of the insertion head and can be deployed, by gripping the housing and sliding the two housing halves together, such that it is possible to apply the insertion head by inserting the puncture needle and the cannula into the body of a patient. After application is completed, the puncture needle can be removed from the cannula and from the cannula housing carrying the latter, by the two housing halves, with the puncture needle held thereon, being moved away from the body counter to the direction of insertion. In doing so, the puncture needle is held in the housing such that, directly after emerging from the cannula housing, it is automatically pivoted back by a spring force into a protected position in the housing.

In one embodiment, the insertion head according to the present invention comprises a housing with a first housing part and a second housing part, which are movable relative to each other. In some preferred embodiments, the housing is designed as a grip, with the first housing part forming a first grip component and the second housing part forming a second grip component.

In some embodiments, the insertion head further comprises a base and a flexible insertion device, which is stabilized by a puncture device, to prevent the insertion device from buckling during insertion into the tissue. The insertion device can be designed, for example, as a flexible cannula (soft cannula) and can be stabilized by a flexurally stiff or substantially rigid puncture device, for example a stiff cannula or needle, during insertion into the tissue, for example by said puncture device extending through it. In some preferred embodiments, the insertion device is elongate in the direction of insertion, and slender.

In some embodiments, the insertion device and the puncture device stabilizing it are mounted so as to be jointly movable, within the boundaries of the housing, for example by the insertion device and/or the puncture device being mounted movably in one of the two housing parts. They are mounted in such a way that the insertion device and the puncture device can be moved relative to the housing from a protected position, in which their free ends, provided for puncturing organic tissue are arranged inside the boundaries of the housing and/or base to avoid accidental contact with the user or the environment, to an insertion position in which the free ends protrude from the boundaries of the housing and/or the base in such a way that they can be introduced into the organic tissue.

In the protected position, therefore, it is difficult or impossible for a user to accidentally come into contact with the insertion device and the puncture device, such that, in this state, injury to the user and contamination of the insertion device and puncture device during handling of the insertion head are reliably avoided. In some preferred embodiments, in the protected position the insertion device and the puncture device are located with their full length within the boundaries of the housing and are completely screened off, and concealed from view. In some preferred embodiments, the insertion device and the puncture device in the protected position lie at least substantially parallel to an outside face of the housing. This favors a flat design of the insertion head, its height being measured at right angles to the outside face.

In the insertion position, in which the insertion head is ready for application, the free ends of the insertion device and of the puncture device protrude beyond the boundaries of the housing, beyond its underside. However, it is also possible in principle for them to protrude from another side of the housing, as long as they protrude far enough to permit penetration into the tissue. In some preferred embodiments, the insertion device protrudes beyond the underside of the housing by a length adapted for subcutaneous applications, e.g. directly down, away from or out of the underside. For applications within the skin or in intramuscular tissue, the insertion device is correspondingly shorter or longer. Insertion device is to be understood as the lengthwise section that penetrates into the tissue when the insertion head is properly applied.

In some embodiments, the insertion head according to the present invention further comprises a mechanical coupling, by which a movement of the two housing parts or grip components relative to each other is converted into a movement of the insertion device and of the puncture device, in such a way that the insertion device and the puncture device can be moved jointly from the protected position to the insertion position by moving the two housing parts relative to each other.

In some embodiments, the base, at least in the insertion position, provides an underside that can be placed on the organic tissue, e.g the underside of the housing, which underside can also be coated with or formed by a plaster, an adhesive pad or an adhesive layer for affixing to the surface of the tissue, and is penetrated, in the insertion position, by the insertion device and the puncture device in such a way as to permit puncturing and insertion into the tissue, with the base placed with its underside on the tissue.

In some embodiments, the insertion head is also designed such that, in the insertion position, the puncture device is connected or connectable to the housing and releasable from the insertion device such that, after insertion of the insertion device and of the puncture device into the tissue, it is possible, by gripping the housing with one hand and moving it with the hand in a direction counter to the direction of insertion, to remove the puncture device from the base and from the insertion device. For this purpose, provision is made, for example, for the puncture device to have lock or locking means which, at the end of the movement from the protected position to the insertion position, i.e. when the insertion position is reached, locks with or connects to an associated lock or locking means on the housing and thereby generates a form-fit engagement counter to the direction of application, whereas at least in the application position the connection between insertion device and puncture device is only effected by a force fit in the direction counter to the direction of application, e.g. as a result of the friction of the puncture device, designed as puncture needle, in a septum of a cannula housing assigned to the insertion device.

In some embodiments, the insertion head according to the present invention further comprises restoring means by which, directly after removal from the base and from the insertion device, which is done by gripping the housing with one hand and moving it in a direction counter to the direction of insertion, the puncture device can be moved back automatically to a protected position in which the free end of the puncture device is arranged inside the boundaries of the housing. Thus, the possibility of the user accidentally coming into contact with the now contaminated insertion device is reliably prevented. In some preferred embodiments, directly after release from the base and insertion device, the puncture device is brought forcibly to the protected position, without possibly affecting the user, e.g. by being pulled back or pivoted back automatically under the action of a spring. Alternatively, it may be preferred that the automatic movement back to the protected position can be effected primarily by actuation of a trigger member using the hand that is holding the housing, in other words without having to put down the housing together with the puncture device held thereon or without having to use the other hand. In some preferred embodiments, a release button is provided which can be depressed using a free finger of the hand that is holding the housing, or if the automatic return to the protected position is triggered by renewed movement of the two housing parts or grip components relative to each other in a direction in which they have already been moved relative to each other, to effect the movement of the insertion device and puncture device from the protected position to the insertion position. Thus, an insertion head according to the present invention is easy and safe to use.

In some embodiments, the insertion head is provided for a medical or pharmaceutical application, including a cosmetic application. At least the underside of the base is made compatible with tissue. In some preferred embodiments, the insertion head is a component of an infusion set for administering insulin, an analgesic or another medicament that can be administered by infusion. Instead of being designed for administration of a medicament or in principle of another administrable product, the insertion head can also be used for diagnostic purposes. In such applications or uses, the insertion device can carry a sensor, for example for measuring glucose concentration in a body fluid or another physical and/or biochemical parameter that is or may be crucial to the state of health of a patient. The insertion head can also be formed as a perfusion device for diagnostic purposes. In such a design, after the insertion device has been introduced into the tissue, it is flushed through by an irrigation liquid which takes up one or more defined constituents of the body fluid, to permit analysis of the irrigation liquid supplemented by the relevant constituent or several constituents of the body fluid.

In some embodiments, the insertion head can form a combined device in accordance with the present invention for administration of a product and diagnosis. The insertion device can be formed for delivering a product, e.g. a medicament of an irrigation liquid, or for withdrawing a body fluid or just one or more defined constituents of a body fluid, i.e. the insertion device forms at least one cross section of flow in such an application. The insertion device can also serve in combination for delivery and withdrawal of substances. If the insertion head is formed only as a measurement device, then it can also be used simply to place a sensor or a part of a sensor into position, i.e. can serve purely as a mechanical application device. In a further development as measurement device, it can serve not only for mechanical application but also for transferring control signals to the sensor and/or measurement signals from the sensor. In combined applications, it can also comprise at least one cross section of flow for substance transport, i.e. a flow conduit, and at least one signal line. The signal line can be omitted if the sensor is designed for wireless reception of control signals and/or for wireless transmission of measurement signals. In some embodiments, the insertion device can also have two or more insertion devices with associated puncture devices that protrude separately. Thus, a first insertion device can be used for transporting substance into the tissue, and another for transporting substance out of the tissue, or simply for applying a sensor or part of a sensor. With several insertion devices that each have a cross section of flow, it is also possible for different substances to be administered with the same insertion head. This can also be done with an insertion device that forms several separate cross sections of flow within a common area.

In a preferred embodiment of the insertion head, the two housing parts can be gripped between two fingers of one hand, thus forming a first grip component and a second grip component, and, with one finger pressing against one of the housing parts, the second housing part can be moved in the direction of the first housing part, to cause the movement of the insertion device and puncture device from the protected position to the insertion position. In this way it is possible for the insertion head according to the present invention to be used easily and safely without further auxiliary means such as a specially adapted inserter.

In some preferred embodiments, the first of the two housing parts movable relative to each other is connected immovably to the base. In principle, however, both of the housing parts movable relative to each other can also be movable relative to the base and, in particular, are connected to the base and movable relative to the latter.

For transmitting the relative movement of the two mutually movable housing parts to the insertion device and to the puncture device, a rigid coupling can be provided, i.e. one of the two housing parts and the insertion/puncture device can be rigidly connected to each other, by which is also meant that they may originally be made in one piece. For example, in the case of pivotability of the insertion device and puncture device relative to the base, a rigid coupling can be readily achieved if the housing part joined rigidly to the puncture device is also able to pivot relative to the base. Compared to the insertion head of German patent application No. 10 2004 039 408.3, the insertion head according to the present invention has the advantage that the other of the two mutually movable housing parts can serve as an abutment for the user, and the force that is to be applied for the pivoting movement does not have to be taken up by the tissue via the base. If the user is in possession of a suitable inserter, with which the insertion head is placed on the tissue and the insertion device is inserted into the tissue, this force is taken up inside the inserter.

In another preferred embodiment of the insertion head, the base is connected immovably to the insertion device such that, upon movement of the latter from the protected position to the insertion position, it is moved along with it. In this way, the connection between insertion device and base can be produced easily and therefore inexpensively.

In an alternative embodiment to the preceding one, with the insertion device and puncture device located in the protected position, the underside of the base forms at least a part of an outside face of the housing, e.g. of the underside of the housing, such that, in the protected position, their free ends are set back behind the underside of the base. During their movement from the protected position to the insertion position, the insertion device and the puncture device can be moved relative to the base, such that their free ends protrude or extend beyond the underside of the base in the insertion position. Such embodiments allow the base to be designed as the underside of the housing, thus permitting compact insertion heads according to the present invention. In embodiments in which the housing forms a grip, that is to say the two housing parts form a first grip component and a second grip component, it may be preferred if this grip protrudes down or extends from the base, with the first grip component being immovable relative to the base and the second grip component being movable relative to the first grip component and to the base, e.g. being displaceable or pivotable. The movable second grip component is coupled to the insertion device such that a movement of the second grip component causes a movement of the insertion device into the insertion position. By equipping the grip with a movable grip component, the movement of the insertion device can be effected by grasping and actuating the grip. The grip itself forms the abutment for the movable second grip component. In this sense, the part of the grip forming the abutment is here designated as the first grip component. The second grip component can be designed as a push button, for example. The first grip component can be a housing from which such a push button protrudes. In some preferred embodiments, the two grip components only form the grip together, for example they form the halves of an overall two-part grip.

In yet another preferred embodiment of the insertion head, the insertion device is mounted movably in or relative to the base, i.e. displaceably and/or pivotably therein. This affords the advantage that this mounting arrangement can at the same time form the connection between base and insertion device in the applied state, such that additional connection elements can be dispensed with.

In some preferred embodiments, the base and a hinge element or guide element of a sliding guide together form a hinge or a linear or non-linear sliding guide, and the insertion device protrudes from the hinge element or the guide element. Such a hinge element or guide element could, for example, serve at the same time as cannula housing and could include a path for delivery or withdrawal of liquid from the insertion device.

In embodiments of the insertion head in which the underside of the base forms at least a part of an outside face of the housing when the insertion device and puncture device are in the protected position, it may be preferred that the housing extends upwards from a top face of the base, in other words is arranged above the base.

In yet another preferred embodiment of the insertion head according to the present invention, the two housing parts or first and second grip components are pivotable relative to each other or displaceable, e.g. slideable one inside the other, to effect the movement of the insertion device and of the puncture device from the protected position to the insertion position. It may be preferred that the two housing parts or grip components are linearly displaceable relative to each other to effect this movement.

In embodiments in which the underside of the base forms at least a part of an outside face or underside of the housing when the insertion device and puncture device are in the protected position, it may be preferred if the two housing parts are movable substantially parallel to the underside of the base. This can entail a linear mobility. Such embodiments make it much easier to handle or maneuver the insertion head according to the present invention with one hand, and they permit formation of compact insertion heads according to the present invention.

In yet another preferred embodiment of the insertion head according to the present invention, the insertion device can be pivoted together with the puncture device from the protected position to the insertion position by the movement of the two housing parts or grip components relative to each other. Pivotability can be achieved in an inexpensive manner, permits the provision of compact insertion heads according to the present invention and is also operationally reliable. In some preferred embodiments, at the moment when the insertion device or puncture device pivots with its free end beyond the boundaries of the housing or beyond the underside of the housing or base, the longitudinal axis of the insertion device forms with the underside of the base an acute angle, e.g. an angle of less than 50°. In some preferred embodiments, the angle is less than 30°, such that, at the moment of pivoting out, the longitudinal axis or insertion device is at least substantially parallel to the boundary or underside of the housing or to the bearing surface of the base.

In embodiments of the insertion head in which the insertion device and the puncture device can be pivoted about a rotation axis from the protected position to the insertion position, it may be preferred if the longitudinal axis of the insertion device, which is pivoted about the rotation axis, intersects the rotation axis. If the longitudinal axis of the insertion device does not intersect the rotation axis, but passes it at a distance, the distance is smaller than the length of the insertion device. In some preferred embodiments, the distance is at most half as great as the intended depth of penetration or length of the insertion device. In preferred embodiments, the pivot angle of the insertion device is 90°±10°. In similarly advantageous configurations, however, the pivot angle can also be smaller, e.g. if the insertion device is also pivoted relative to the base and, in the insertion position, is not at right angles to the underside of the base, but instead at an acute angle, e.g., at least 30°. Accordingly, in some preferred embodiments, the pivot angle in these configurations is at least about 30° or any intermediate value between about 30° and about 90°. In principle, the pivot angle can also be greater than 90°.

In some preferred embodiments of the insertion head according to the present invention, the coupling, by which the relative movement of the two housing parts or grip components is converted into the movement of the insertion device and puncture device, is a gear mechanism. Such a coupling has the advantage that the mobility of the housing parts relative to each other does not have to correspond to the mobility of the insertion device, and instead both forms of mobility can each be optimally configured for their own purpose. Thus, the insertion device can be moved by pivoting, and the housing parts can be guided in translation relative to each other, e.g. linearly. In the case of one of the housing parts being pivotable, its pivot axis can be different than that of the insertion device. Whereas the insertion device is pivotable about a rotation axis at least substantially parallel to a boundary or the underside of the housing or of the base, which also applies for some of the embodiments of the insertion head according to the present invention with a pivotable insertion device, it is possible for a pivotable housing part to be pivoted about a rotation axis at least substantially at right angles to this boundary or underside of the housing or of the base. However, a gear mechanism may also be advantageous if, in the case of a pivotable housing part, the latter's rotation axis is spaced apart in parallel from the rotation axis of the pivotable insertion device. In such a case, the pivot angle of the housing part, stepped down or stepped up by a gear mechanism, can be transmitted to the insertion device.

A preferred embodiment of the insertion head according to the present invention with a gear-type coupling comprises a toothed wheel and a toothed rack which are in toothed engagement with each other and mesh with each other during movement of the two housing parts relative to each other, upon movement of the insertion device. The toothed rack is connected to one of the two housing parts such that a movement of this housing part relative to the rotation axis of the toothed wheel in the longitudinal direction of the toothed rack is converted into a rotation movement of the toothed wheel connected in this case to the insertion device. With a very small diameter of the toothed wheel and correspondingly fine teeth or distribution of the teeth, a comparatively short stroke of the housing parts relative to each other can be converted into a rotation movement of the toothed wheel about a considerable part of a full revolution, e.g. a quarter revolution of the toothed wheel. The movable second grip component is advantageously formed in one piece with the toothed rack. In some preferred embodiments, the insertion device may be connected in a rotationally fixed manner to the toothed wheel.

In yet another preferred embodiment of the insertion head according to the present invention, the insertion device and/or the puncture device is held via a rotation shaft or pivot shaft on the base or on a first of the two housing parts. A sliding block is provided, which may be arranged eccentrically and separately with respect to the rotation shaft. A guide slot is also provided, which is operatively engaged with the sliding block such that a movement of the two housing parts relative to each other transfers the sliding block, guided by the guide slot, from a first position, which corresponds to the protected position of the insertion device and of the puncture device, to a second position, which corresponds to the insertion position of the insertion device and of the puncture device. This embodiment permits relatively complex movement patterns and, at the same time, only relatively low forces have to be exerted via the housing parts, and jamming of the individual components of the coupling mechanism is highly unlikely.

In yet another preferred embodiment, the housing is connected releasably to the base. This connection is released automatically during the movement of the two housing parts relative to each other, e.g. during the movement of the two housing parts corresponding to the movement of the insertion device from the protected position to the insertion position, or during a subsequent movement or continuing movement of the two housing parts relative to each other. Alternatively, however, it would also be conceivable in principle to equip the housing or the base with another movable component, whose actuation releases the connection to the base. The connection between the housing and the base can be created by purely frictional engagement, but in some preferred embodiments it is afforded exclusively by a form fit or a combination of a form fit and a frictional fit. To create the connection, the base and the housing, e.g. one of the housing parts, are each equipped with at least one connection element, these connection elements being in engagement with each other when the connection exists. To be able to release the connection, at least one of the connection elements can be moved out of the engagement counter to a restoring elasticity force. In some preferred embodiments, one of the two housing parts, which is movable relative to the base, serves not only to transfer the insertion device to the insertion position, but also to release the connection, by virtue of the fact that during its movement this housing part, by contact, e.g. sliding contact, moves, for example elastically bends, one of the connection elements out of engagement counter to the elasticity force.

In embodiments of the insertion head according to the present invention with a coupling comprising a guide slot and a housing connected releasably to the base, a movement of the two housing parts relative to each other along a first distance of a first portion of the guide slot transfers the sliding block, guided by the guide slot, from a first position, which corresponds to the protected position of the insertion device and of the puncture device, to a second position, which corresponds to the insertion position of the insertion device and of the puncture device. Moreover, a connection element is provided which connects the base reversibly to the housing and, to release the housing from the base, precisely one of the two housing parts can be moved relative to the base along a second distance perpendicular to the direction of extent of the insertion device located in the insertion position, the guide slot having a second portion corresponding to the second distance, such that the insertion device is not entrained in the release movement. In other words, with a suitable design of the guide slot, it is possible, for example, after entry of the puncture device and of the insertion device into the body of a patient, to move the housing or one of the housing parts parallel to the surface of the body or to the surface of a plaster securing the base on the body of the patient, without this straining the organic tissue. In this way, separation of the housing from the base, and thus of the puncture device from the insertion device, is advantageously possible by actuating the same components, e.g. of the two housing parts relative to each other, to effect both the movement of the insertion device and of the puncture device into the insertion position and also the uncoupling of the housing from the base. It is also possible for the movement and the uncoupling to be effected in direct succession. Here, the sliding block runs or extends through the entire guide slot, as a result of which the cannula or insertion device is already pivoted out in conjunction with the puncture needle or puncture device, and at the same time, or immediately thereafter, the housing is uncoupled from the base, before the cannula is applied with the needle. There then remains only an easily detachable join between the section of the insertion head according to the present invention remaining in or on the patient's body (base, cannula) and the section thereof (puncture needle, housing) that is to be removed.

In yet another preferred embodiment of the insertion head, the puncture device in the protected position is not yet connected to the housing, but connects automatically to the housing during the movement into the insertion position. For this purpose, the end of the insertion device directed away from its free end can be provided with a connection element, e.g. a snap-fit element, which, simultaneously with the completion of the movement into the insertion position, or shortly before, comes into connecting engagement with a mating connection element of the housing. Although the connection can in principle be a purely frictional connection, it may include at least one form-fit connection. The connection element of the puncture device can establish a snap-fit connection with the mating connection element. For a form-fit connection, it also suffices in principle for it to be engaged from behind with respect to the direction in which the housing is to be removed from the insertion device or from the base; an elastic snap-fit engagement is therefore not absolutely essential.

Thus, for example in the aforementioned embodiment, one of the two housing parts can be pushed so far into the other housing part that, upon completion of the movement of the insertion device from the protected position to the insertion position, a control ramp on one of the two housing parts can abut against a deflector ramp on a connection element which connects the base reversibly to the housing, to deflect a connection device from its engagement position, such that the grip and the base can be separated. This embodiment is advantageous, in conjunction with the second distance of a guide slot as has already been described, since it allows the insertion head according to the present invention to be converted from the puncture function to the delivery function, for delivery of a medicament, without placing a strain on the patient's tissue.

In yet another preferred embodiment of the insertion head, at least the free ends of the insertion device and of the puncture device, or the entire insertion device and the entire puncture device, are received in a seat in the protected position, said seat being formed either by the base or by the housing. If the housing forms the seat, the base can form a partial seat which is received in the seat formed by the housing, provided that, in the case of the releasable housing, the latter is connected to the base.

In yet another preferred embodiment of the insertion head, the insertion device is assigned a securing structure, which reversibly retains the insertion device and puncture device in the protected position. For example, one of the two housing parts can be designed with a locking shoulder, which can be brought into reversible engagement with a complementary locking member on the other housing part. When a resistance is overcome, a relative movement of the two housing parts can take place, and the insertion device (cannula) with puncture device (puncture needle) can be driven or pivoted into the insertion position (application position).

The insertion device can advantageously be assigned a cannula housing which is moved along with the insertion device, said cannula housing comprising the securing structure. The latter is intended to lie opposite a wall of one of the two housing parts extending parallel to the direction of movement of the two housing parts. In this way, it is possible for an engagement element on the inside face of the wall to engage reversibly with the securing structure in the protected position of the insertion device. By these measures, it is possible to keep the insertion device together with the puncture device safely in the seat in the protected position and, after an initial resistance provided by the securing structure and the engagement element has been overcome, to move the two housing parts relative to each other and thereby bring about the desired movement of the insertion device in conjunction with the puncture device from the protected position to the insertion position.

Another preferred embodiment of the insertion head according to the present invention is one in which, in one of the two housing parts and/or in the other of the two housing parts that receives the insertion device and puncture device in the protected position, a securing slot is provided in which the puncture device can be locked in a seat after the removal of the housing and of the puncture device from the insertion device and base and after the reverse movement into the protected position. Because of its resiliency, the tip of the puncture device can be elastically deformed and laterally deflected along the guide slot when pivoting back into the protected position or into the seat, and can then lock, e.g. irreversibly, in a securing recess behind a securing shoulder. In this position, it is then held safely in the protected position. The securing slot can also be provided on various other components of the insertion head that are not removed upon removal of the puncture device from the insertion device and the base.

In yet another preferred embodiment of the insertion head, the puncture device is assigned a retainer element which, during the automatic reverse movement of the puncture device to a protected position, is moved along with the puncture device, said retainer element having a locking shoulder which, upon the automatic reverse movement in the housing comes into locking engagement with an engagement element to prevent the puncture device from moving out of the housing again.

In yet another preferred embodiment of the insertion head, the insertion head is designed for automated placement on the tissue by what may be though of or called an inserter. For this purpose, the insertion head, e.g. its housing, has a retaining structure which can be brought into retaining engagement with the retainer device of the inserter. If, as may be preferred, one of the two mutually movable housing parts of the insertion head is connected immovably to the base, and the other of the two housing parts is movable relative to the base, the immovable housing part forms the retaining structure. In some preferred embodiments, the retaining structure is formed in one piece with the housing or on the housing part immovable relative to the base, or is at least rigidly connected to the housing or the housing part.

BRIEF DESCRIPTION OF THE DRAWINGS

FIG. 4 is a view similar to FIG. 3, with the puncture device arranged in the protected position again;

FIG. 5 shows an embodiment of an upper portion of a first housing part of a second embodiment of an insertion head according to the present invention, in horizontal section;

FIG. 6 is a side view of a second housing part that can be pushed into the first housing part whose upper portion is shown in FIG. 5;

FIG. 17 shows the insertion head according to FIGS. 15 and 16, with the grip and puncture device separated from the base and insertion device;

FIG. 18 is a side view of the first and second grip components, in the state when released from the base;

FIG. 19 is a sectional view of an insertion head with the insertion device located in the protected position, FIG. 19a is a detail from FIG. 19, likewise in a sectional view;

FIG. 20 shows the insertion head according to FIG. 19 with the insertion device located in the insertion position, likewise in a sectional view;

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Identical or at least functionally identical components are generally designated herein by identical or comparable reference signs, such that repeated descriptions can in most cases be dispensed with. Unless otherwise indicated, the components of the individual embodiments are for the most part interchangeable, i.e. can be combined with one another. Further features, objectives and advantages of the present invention will become apparent from the embodiments described herein.

Figure 1:
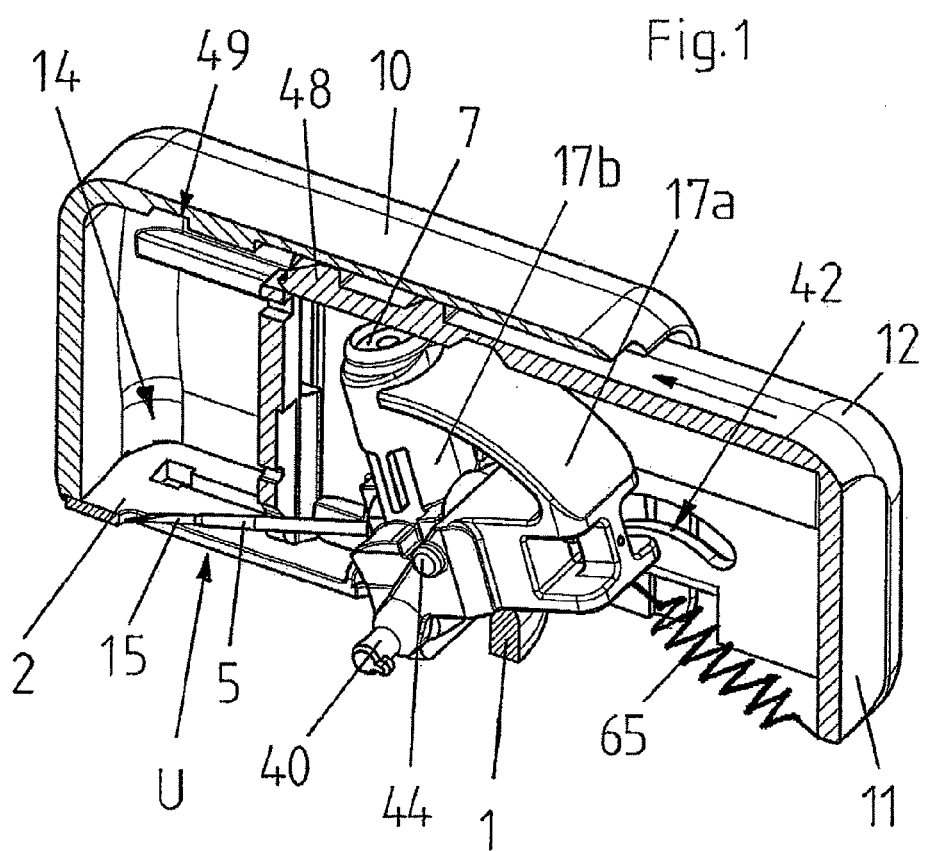
FIG. 1 is a vertical section through a first embodiment of an insertion head according to the present invention, with the insertion device and puncture device arranged in a protected position.

FIG. 1 shows a first preferred embodiment of an insertion head according to the present invention in longitudinal section. The insertion head comprises a base which is formed in one piece from plastic. The base can be placed with its underside U onto organic tissue. The insertion head further comprises a housing made up of two housing parts 10, 12 which can be moved relative to each other and which form a two-part grip with a first grip component 10 and a second grip component 12. The first grip component 10 is connected immovably, but releasably, to the base. The second grip component 12 is held movably on the first grip component 10, said second grip component 12 being linearly displaceable relative to the first grip component 10 and also to the base. The axis of the mobility of the second grip component 12 lies parallel to an underside U of the base. The direction of the mobility is indicated by an arrow on the top face of the second grip component 12.

In the first grip component 10, an insertion device 5 is mounted so as to be pivotable relative to the base about a rotation axis parallel to the underside U of the base. The insertion device 5 is elongate. In the illustrative embodiment, it is designed as a flexible cannula 5. The insertion device 5 has a puncture device 15 extending through it, which puncture device is designed as a thin needle 15 whose flexural stiffness is sufficient to allow the puncture device 15, together with the insertion device 15 snugly enclosing it, to be introduced through the surface of the skin into subcutaneous tissue and thereby introduce the insertion device 5. In preferred embodiments, the underside U of the base is provided with an adhesive pad for affixing the insertion head on the tissue, preferably the surface of the skin.

The pivotability of the insertion device 5 together with the puncture device 15 is provided for by a retainer element 17a, which on two opposite sides forms in each case a shaft stump or base component 40 of a pivot hinge. The axes of the shaft stumps 40 coincide. The first grip component 10 forms the bearings for the shaft stumps 40 in the form of bushings or, if appropriate, also in the form of open eyelets.

The puncture device 15 is connected securely to the retainer element 17a, while the cannula 5 is connected securely to a cannula housing 17b, which has a delivery piece 7 for a liquid medicament, for example insulin. The delivery piece 7 protrudes from the cannula housing 17b approximately at right angles to the longitudinal axis of the insertion device 5. In a continuation of the longitudinal axis of the cannula 5, the cannula housing 17b has, at its end directed away from the cannula 5, a septum 58 (shown in FIG. 3) which is penetrated by the puncture needle 15. In this way, the cannula 5 and the cannula housing 17b are connected with a force fit to the retainer element 17a and the puncture needle 15 held thereon, and, by turning the retainer element 17a, they can be pivoted about the rotation axes of the shaft stumps 40 as a unit (comprising components 5, 6, 7, 15, 17b).

As can also be seen, the movable second grip component 12 is provided, on each of its two long sides, with a guide slot 42 in which in each case a stud-shaped sliding block 44 of the retainer element 17a engages. Because of the cross-sectional view, only one of the two guide slots 42 is shown, and only one of the sliding blocks 44 can be seen, because the other one is concealed in this view by the retainer element 17a.

When the second grip component 12, movable relative to the base, is pushed in the direction of the directional arrow into the first grip component 10, fixed relative to the base, with the first grip component 10 guiding the second guide component 12 in this movement, the guide slots 42 are displaced along the sliding blocks 44 such that the displacement movement of the second grip component 12 is converted into a rotation movement of the retainer element 17a about the axes of the shaft stumps 40 and thus into a pivoting movement of the insertion device 5 and of the puncture device 15 and also of the delivery piece 7 about these axes.

Figure 2:
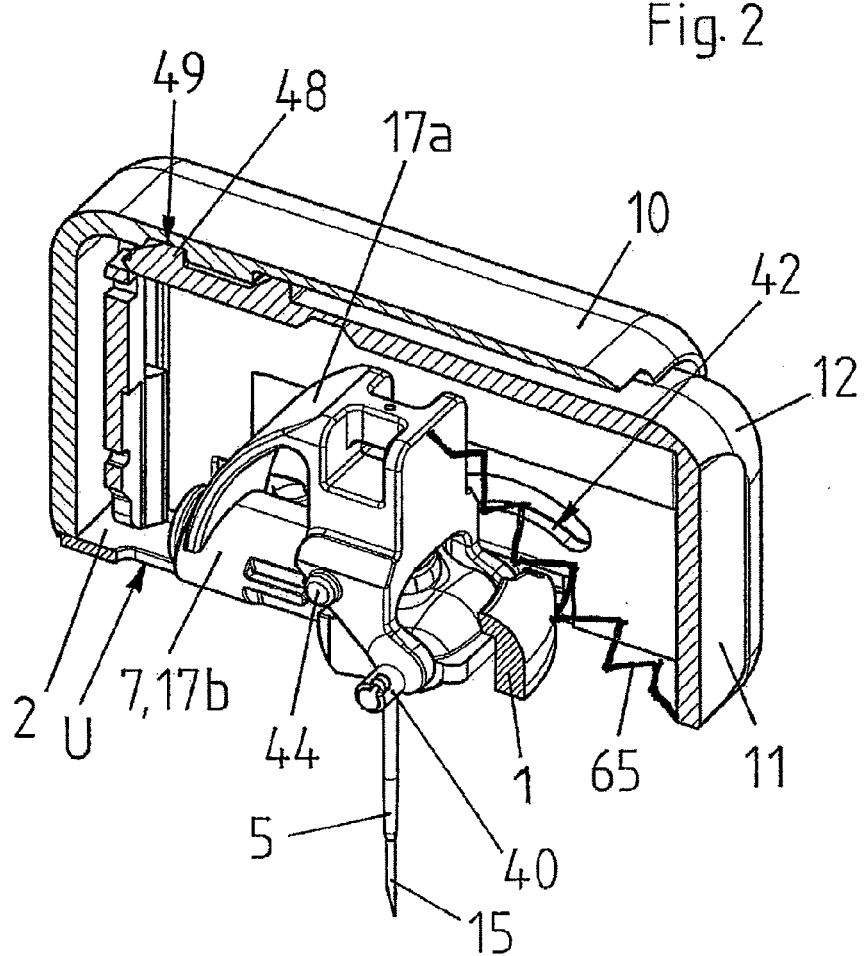
FIG. 2 is a longitudinal section through the insertion head from FIG. 1, with the insertion device and puncture device arranged in the insertion position.

The pivoting movement, which transfers the insertion device 5 and the puncture device 15 from their protected position shown in FIG. 1 to the insertion position shown in FIG. 2, takes place counter to the spring force of a compression spring 65, which is arranged between the retainer element 17a and the second grip component 12 and which is increasingly pretensioned as the pivoting movement increases.

In the protected position, the insertion device 5 and the puncture device 15 are at an angle of approximately 10° with respect to the underside U of the base. The insertion device 5, and the part of the puncture device 15 protruding in the same direction from the retainer element 17a, are received, in the joint protected position, in a seat area 14 substantially enclosed by the first grip part 10 and the base. With the insertion device 5 and puncture device 15 located in the protected position, this ensures that the user cannot injure himself on the puncture device 15 and, conversely, that the insertion device 5 and the puncture device 15 cannot be damaged or contaminated by careless handling. Since the base has only a narrow slit for passage of the insertion device 5 and puncture device 15, the seat 14 here also forms a screen, such that the user cannot see the puncture device 15 from the top of the insertion head or from side on. An adhesive pad provided on the underside of the base is likewise provided with a slit for passage of the insertion device 5 and the puncture device 15.

To introduce the insertion device 5 into the body tissue to a point below the skin or, if appropriate, only into the skin, the user grips or takes hold of the insertion head via the grip between thumb and index finger. The grip components 10 and 12 are each provided with a suitably formed lateral grip surface 11. By pressing the grip components 10 and 12 together, as has already been described, the guide slots 42 are displaced in the side walls 44 of the retainer element 17a, such that the insertion device 5 and the puncture device 15 are pivoted into the insertion position shown in FIG. 2. When this position is reached, the two grip components 10, 12 lock irreversibly with each other, by a locking lug 48 formed on the second grip part 12 engaging resiliently in a corresponding undercut 49 formed on the first grip component, such that they cannot be moved apart again. At the same time, the first grip component 10, which in the situation shown in FIG. 1 is connected immovably but releasably to the base, is released from the base by the second grip component 12 being pushed into the first grip component 10, since resilient locking lugs (not shown) formed on the first grip component 10 are disengaged from corresponding mating elements on the base. In this state, the grip, the retainer element 17a and the puncture device 15 are connected to the base, the insertion device 5 and the cannula housing 17b only by the friction existing between the puncture device 15 and the septum 58 of the cannula housing 17b.

Similarly, when the insertion position is reached, the cannula housing 17b is locked irreversibly by locking means (not shown) to the base, such that both components can be connected fixedly and irreversibly to each other in the insertion position. The manner in which such locking means can be configured, for example in the form of resilient locking lugs that lock into corresponding undercuts, is known to persons skilled in the art and does not therefore have to be discussed in detail here.

In the present case, the distance of the sliding blocks 44 from the pivot axis, and the curves of the guide slots 42, are chosen such that a displacement of the second grip component 12 by a few millimeters, for example 4 or 5 millimeters, causes a pivoting movement of the insertion device 5 and of the puncture device 15 from the protected position to the insertion position about a pivot angle of approximately 80°, whereupon the insertion device 5 and the puncture device 15 in the insertion position protrude approximately at right angles from the underside U of the base.

To place the insertion head on a tissue surface and to introduce the insertion device 5 into the tissue, the user holds the insertion head by the grip and moves it onto the tissue surface. In doing so, the puncture device 15 pierces the tissue surface, preferably human skin, and penetrates into the skin. The snugly enclosing insertion device 5 penetrates together with the puncture device 15, until the insertion head lies with its underside U, i.e. with the underside U of the base, on the tissue surface and is fixed, for example adhesively, to the skin surface, preferably by a layer of adhesive or by an adhesive pad.

To administer the medicament after the insertion head has been placed on the tissue, the grip with the retainer element 17a and puncture device 15 has to be removed, and the delivery piece 7 has to be connected, via a connector cooperating with the delivery piece 7, to a medicament reservoir, e.g. a medicament pump.

To do this, the grip is grasped in one hand and is moved away from the base counter to the direction of insertion of the insertion device 5 into the tissue, as a result of which the puncture device 15 is pulled out of the insertion device 5 and cannula housing 17b and frees the cross section of flow through the insertion device 5. The entry opening for the puncture device 15 into the cannula housing 17b, which was formed by a septum 58, is closed by the septum 58 after withdrawal of the puncture device 15. When the puncture device 15 is pulled out of the insertion device 5, the cross section of flow of the insertion device 5 is automatically connected fluidically to the delivery piece 7. In this regard, the insertion head can be designed in the manner described, for example, in DE 198 21 723 C1 and DE 10 2004 039 408.3.

Figure 3:
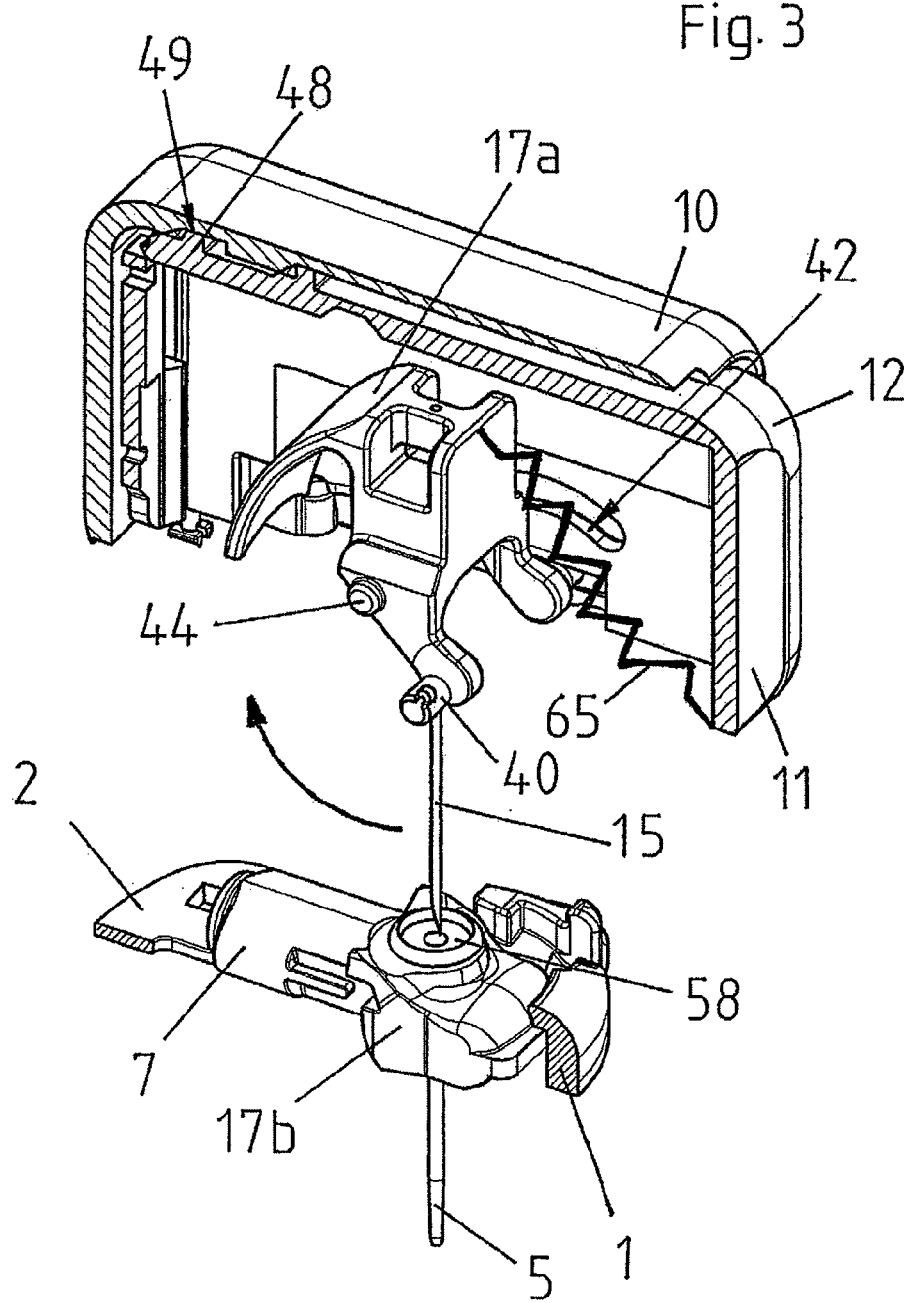
FIG. 3 is a longitudinal section through the insertion head from FIG. 1, during removal of the puncture device after application.

FIG. 3 shows the two assembly groups of the insertion head released from each other, namely, in the first instance, the base with cannula housing 17b and insertion device 5, and, secondly, the grip with retainer element 17a and puncture device 15, and in a mutually oriented position in which the longitudinal axis of the insertion device 5 and the longitudinal axis of the puncture device 15 are in alignment with each other.

Directly after the puncture device 15 has left the septum 58, it is automatically pivoted back into the protected position, together with the retainer element 17a mounted in the second grip component 12, by the pretensioned compression spring 65 (this pivoting movement being indicated by a directional arrow in FIG. 3), such that it is once again arranged inside the boundaries of the housing formed by the two grip components 10, 12. This situation is depicted in FIG. 4.

The base 2 and cannula housing 17b shown in FIG. 3, with the cannula 5 secured thereon, remain on the tissue surface and in this sense form an indwelling part. By contrast, the grip with the puncture device 15 arranged in the protected position and held by the retainer element 17a, is discarded. The indwelling part can thus be made advantageously flat and does not show when worn under clothing. The flexibility of the insertion device 5 is such that the insertion device 5 does not cause any discomfort in the inserted state, but it is still sufficiently stable to reliably ensure supply of the medicament.

FIG. 5, in a perspective horizontal section obliquely from below, shows the upper portion of a second insertion head according to the present invention made up of two housing parts 10, 12 that can slide one inside the other. This is the upper portion of the first, outer housing part 10, into which the second, inner housing part 12, which is shown in a perspective side view in FIG. 6, is at least partially pushed when the insertion head is fully assembled. Apart from the differences explained below, the second insertion head according to the present invention has practically the same structure and the same functions as the insertion head shown in FIGS. 1 to 4. A difference from the previously described insertion head is that, in the present embodiment here, after the two housing parts 10, 12 have been pushed together and have caused the insertion device and the puncture device to pivot out from the protected position to the insertion position, they are temporarily interlocked in the pushed-together position, representing the insertion position, by a so-called "ballpoint pen mechanism", and, after application of the insertion device and subsequent separation of the housing parts 10, 12 with puncture device 15 from the insertion device 5, base and cannula housing 17b, which remain at the application site, the two housing parts 10, 12 are pressed further together in the direction of sliding together and are then released, whereupon they are pushed apart again by the force of a compression spring 66 that is increasingly pretensioned during the sliding together (see FIGS. 7 to 9), and the insertion device is then pivoted automatically back into a protected position inside the boundaries of the housing formed by the two housing parts 10, 12.

Figure 7:
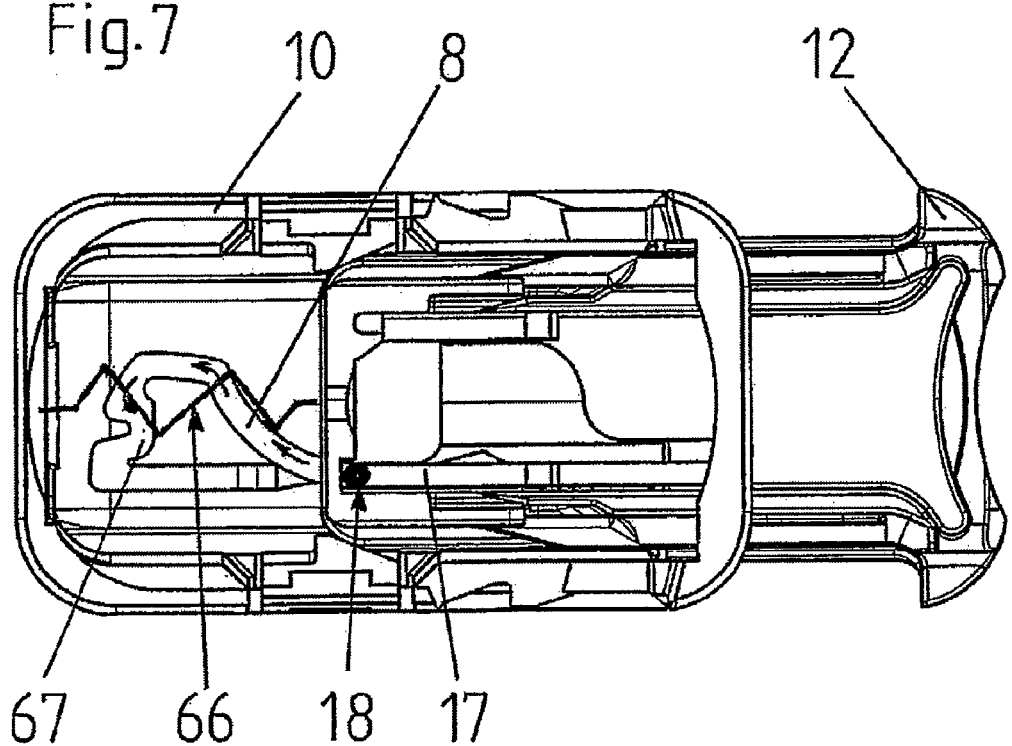
FIG. 7 is a bottom view of the two housing parts from FIGS. 5 and 6 when arranged in one position relative to each other.
Figure 8:
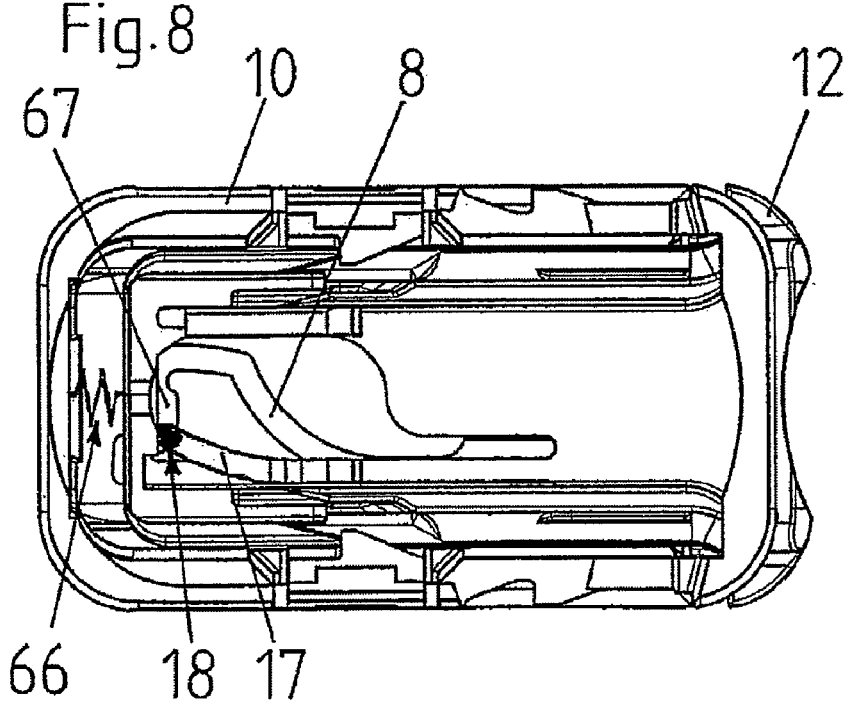
FIG. 8 is a bottom view of the two housing parts from FIGS. 5 and 6, in a situation in which they are pushed together and locked on each other.
Figure 9:
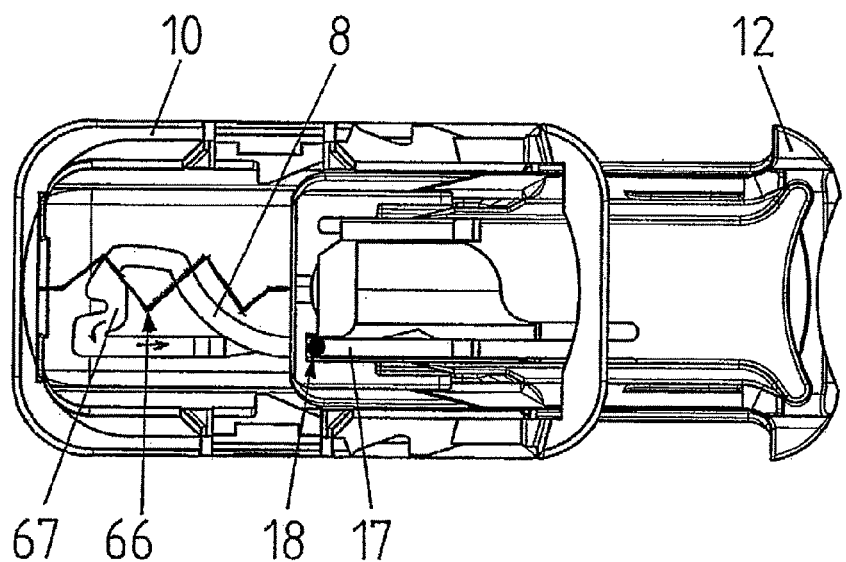
FIG. 9 is a bottom view of the two housing parts from FIGS. 5 and 6 when, after being pressed together again and subsequently released, they are once more arranged relative to each other in the position shown in FIG. 5.

To obtain this "ballpoint pen mechanism", the first housing part 10 has a guide groove 8 on the underside of its upper boundary wall, and a guide cylinder 18 supported by a resiliently elastic arm 17 on the top face of the second housing part 12 engages in said groove 8 and is guided in the latter as the two housing parts 10, 12 are pushed together. By comparing FIGS. 7 and 8, which show a bottom view of the two housing parts 10, 12 without insertion device, puncture device, base and cannula housing, firstly in a basic position that corresponds to the protected position of insertion device and puncture device (FIG. 7) and, secondly, in a position in which they are pushed together substantially completely, corresponding to the insertion position of insertion device and puncture device (FIG. 8), it will be seen that, when the two housing parts 10, 12 are pushed together counter to the force of the compression spring 66, the guide cylinder 18, whose position is indicated in FIGS. 7 to 9 in the form of a black dot for better clarity, is displaced horizontally counter to the spring force of the resiliently elastic arm 17 into a rear hollow 67 of the guide groove 8 (see arrows in FIG. 7), in which it is locked by the force of the compression spring 66 after release of the two housing parts 10, 12 (FIG. 8). In this way, with the insertion head fully assembled, the insertion and puncture device, which is pivoted from the protected position to the insertion position via the mechanical coupling, is also locked in the insertion position, and the insertion head is thus made ready for application.

After application of the insertion head by introducing the insertion device and the puncture device into tissue, and after removal of the two housing parts 10, 12, with the puncture device secured thereon, from the components of the insertion head that remain on the application site, the locking of the guide cylinder 18 in the hollow 67 is cancelled by once again pressing the two housing parts 10, 12 together, since by doing so the spring force of the resiliently elastic arm 18 moves the guide cylinder 18 into another portion of the guide groove 8, along which portion it is guided back to the starting position as a result of the housing parts 10, 12 being pushed apart by the force of the compression spring 66, at the same time as which the puncture device is pivoted back into its protected position (see arrows in FIG. 9). In this state, with the contaminated puncture device protected against access, the housing can be disposed of without any problem and without any risk of injury.

Figure 10:
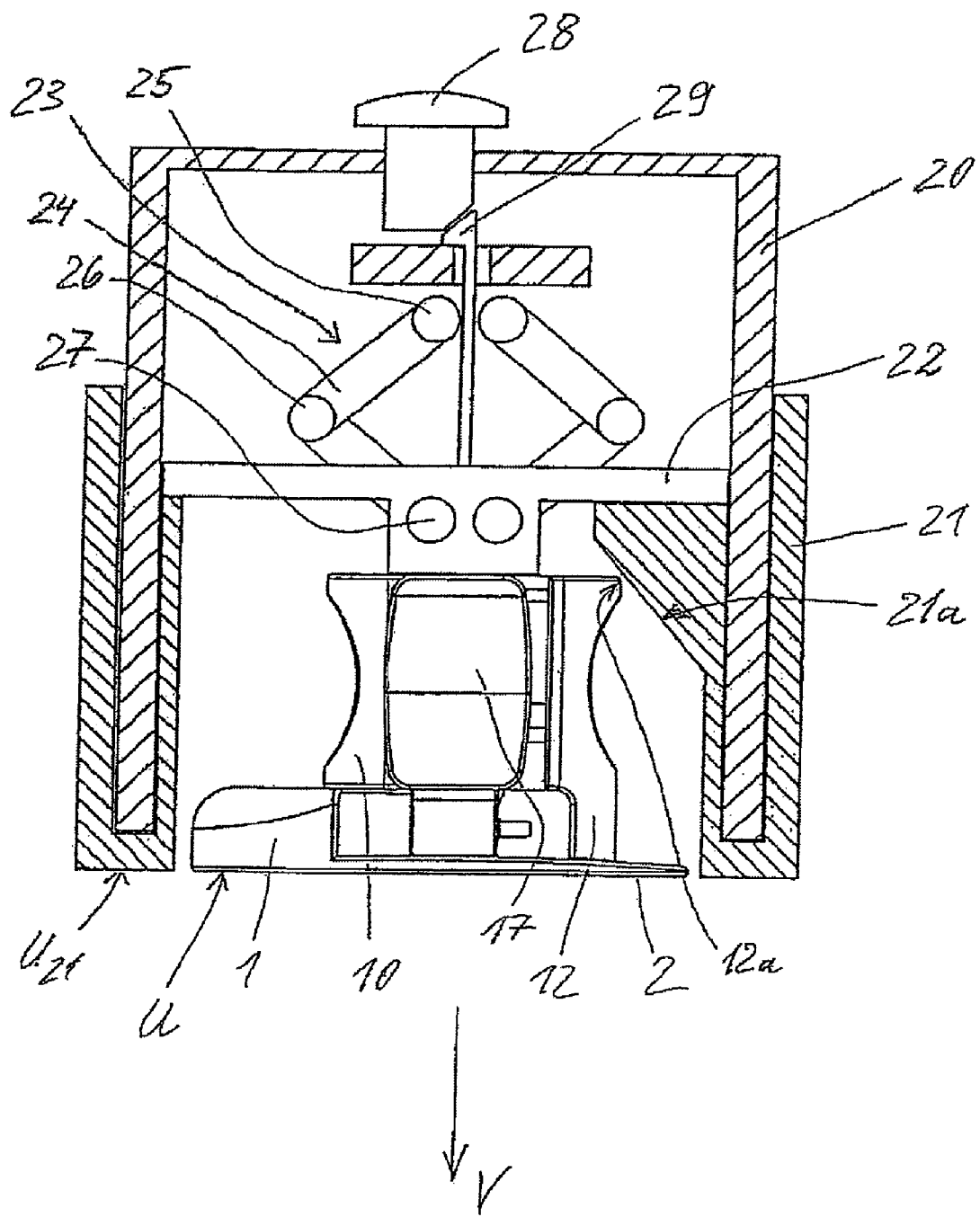
FIG. 10 shows an embodiment of a system in accordance with the present invention, the system comprising an embodiment of an insertion head and an embodiment of an inserter, prior to actuation.

FIG. 10 shows a system consisting of an insertion head according to the present invention, similar to the one shown in FIGS. 1 to 9, and of a specially adapted inserter, which serves to place the insertion head on the tissue such that the user does not have to hold the insertion head between the fingers during placement thereof. In particular, during transfer of the insertion device 5 and puncture device 15 to the insertion position, the user does not hold the insertion head via the grip. This activation of the insertion head is effected with the aid of the inserter. The user is therefore better protected against stick injuries from the puncture device 15, and the insertion device 5 and the puncture device 15 are also better protected against damage and contamination by careless handling, since even when the insertion device and puncture device have been pivoted out into the insertion position, accidental contact with them is prevented by the inserter.

The inserter comprises an inserter housing 20 which is formed as a sleeve part with a base and, viewed from the outside, has substantially the shape of a pot. The inserter housing 20 accommodates a retainer device and a drive mechanism for the insertion head. The retainer device comprises a retainer spring, for example a leaf spring, which holds the insertion head in the starting position, shown in FIG. 10, relative to the inserter housing 20. The retainer spring engages behind a retaining structure 17 formed on the grip. The retention engagement can be released counter to the restoring elasticity force of the retainer spring.

The drive mechanism comprises a thrust element 22 which is arranged in the inserter housing 20 so as to be movable linearly in and counter to a thrust direction V. The thrust direction V coincides with a central longitudinal axis of the inserter housing 20. The drive mechanism further comprises a force generator 23, which acts on the thrust element 22 in the thrust direction V. The force generator 23 comprises two pairs of mutually articulated branches 24, the two pairs of branches 24 being arranged symmetrically with respect to the central longitudinal axis, i.e. symmetrically with respect to the thrust direction V of the inserter housing 20. Each of the pairs of branches is suspended in a pivot hinge 25 fixed in position with respect to the inserter housing 20. The two branches 24 of each respective pair of branches are connected pivotably to each other in a free pivot hinge 26. Moreover, the branch 24 directed away from the positionally fixed hinge 25 is in each case connected to the thrust element 22 in a pivot hinge 27. Springs (not shown), or if appropriate just one spring, tension this arrangement of branches, hinges and thrust element in the thrust direction V. The arrangement composed of branches 24 and hinges 25, 26 and 27 guides the thrust element 22; in addition, or instead of this, the inner jacket surface of the insertion housing 23 could guide the thrust element 22. Moreover, a blocking member 29 is provided which is in blocking engagement with the inserter housing 20, which prevents an advance movement of the thrust element 22. The blocking member 29 can form the blocking engagement with the shell structure formed by the inserter housing 20, or likewise with any other structure fixedly connected thereto with respect to the thrust direction V. The blocking engagement can be released by actuation of a trigger 28 in the form of a push-button.

The inserter further comprises an actuation member 21 which is connected movably to the inserter housing 20 in and counter to the thrust direction V. The actuation member 21 forms a bushing with respect to the inserter housing 20, resulting overall in a two-part, telescopic inserter housing with housing parts 20 and 21.

Because of the difference in function, however, the housing part 21 is designated below as actuation member. The actuation member 21 forms the underside U21 of the inserter, with which the inserter can be and is placed on the tissue surface for placement of the insertion head. In the starting position assumed by the insertion head in FIG. 10, the underside U21 of the inserter and the underside U of the retained insertion head each point in the thrust direction V, which forms at least substantially a surface normal for the two undersides.

The actuation member 21 comprises an outer sleeve part and an inner sleeve part which are connected to each other at the underside U21 and leave an annular gap free between them. The inserter housing 20 protrudes into this annular gap and guides the actuation member 21 in a sliding movement.

In the state shown in FIG. 10, the actuation member 21 assumes a retracted position relative to the inserter housing 20, and the inserter has its shortest length measured in thrust direction V. In this state of the inserter, the insertion head is fitted, i.e. brought into retaining engagement with the retainer device of the inserter. Instead of fitting the insertion head, the inserter can also be pushed over the insertion head lying on a support. The position and geometry of the retainer device is chosen such that the retaining engagement is obtained automatically when the inserter is pushed on. Directly after reception of the insertion head, for example by its being fitted in place, the insertion device 5 of the insertion head is in its protected position. In this sense, the insertion head is still inactive. The inserter is equipped with means, namely the actuation member 21, whose activation moves the insertion device into the insertion position and in this way activates the insertion head.

For this activation, the actuation member 21 and the insertion head together form a joint, in the illustrative embodiment a curved joint. The two joint elements of the joint are a guide curve 21*a*, which the actuation member 21 forms, and an engagement element 12*a* formed by the movable grip component 12. In the coupling via which the actuation member 21 acts on the insertion device 5, the movable grip component 12 forms a receiving member of the insertion head. When the actuation member 21 is moved relative to the inserter housing 20 in the thrust direction V, the guide curve 21*a* slides over the engagement element 12*a*, i.e. over the contact face of the receiving member forming the engagement element 12*a*, i.e. the movable grip component 12. By the pressure contact and the course of the guide curve 21*a* inclined relative to the thrust direction V, the grip component 12 moves transverse to the thrust direction V towards the other grip component 10, and the insertion device 5 pivots, as described as such for the insertion head, into the insertion position. The movable grip component 12 forms the engagement element 12*a* at its upper end directed away from the base 2, in the illustrative embodiment with its outer edge. The guide curve 21*a* is directed towards the underside U21 of the inserter. The inclination is chosen such that the guide curve 21*a*, starting from an end directed away from the underside U21 in the thrust direction V, slopes away from the insertion head or the insertion device 5 pivoted out in the activated state or the central longitudinal axis of the inserter. The angle of inclination is constant, the guide curve 21*a* is a bevel, i.e. an oblique line or surface.

For practical handling, it is recommended that, once the insertion head has been fitted in place, the user holds the inserter with one hand on the actuation member 21, for example by clasping the actuation member 21, and uses his other hand to pull the inserter housing 20 relative to the retained actuation member 21 counter to the thrust direction V. This too is understood as activation of the actuation member. The thrust element 22 and the force generator 23 move together with the inserter housing 20 relative to the actuation member 21. The insertion head held in the starting position by the retainer device is carried along, i.e. also moves relative to the actuation member 21 counter to the thrust direction V. The engagement element 12*a* slides along the guide curve 21*a*. Via this interface based purely on pressure contact, the movable grip component 12 is moved transverse to the thrust direction V, and the insertion device 5 pivots into the insertion position. The insertion head is activated at the end of the excursion movement that the insertion housing 20 and the actuation member 21 execute relative to each other.

Figure 11:
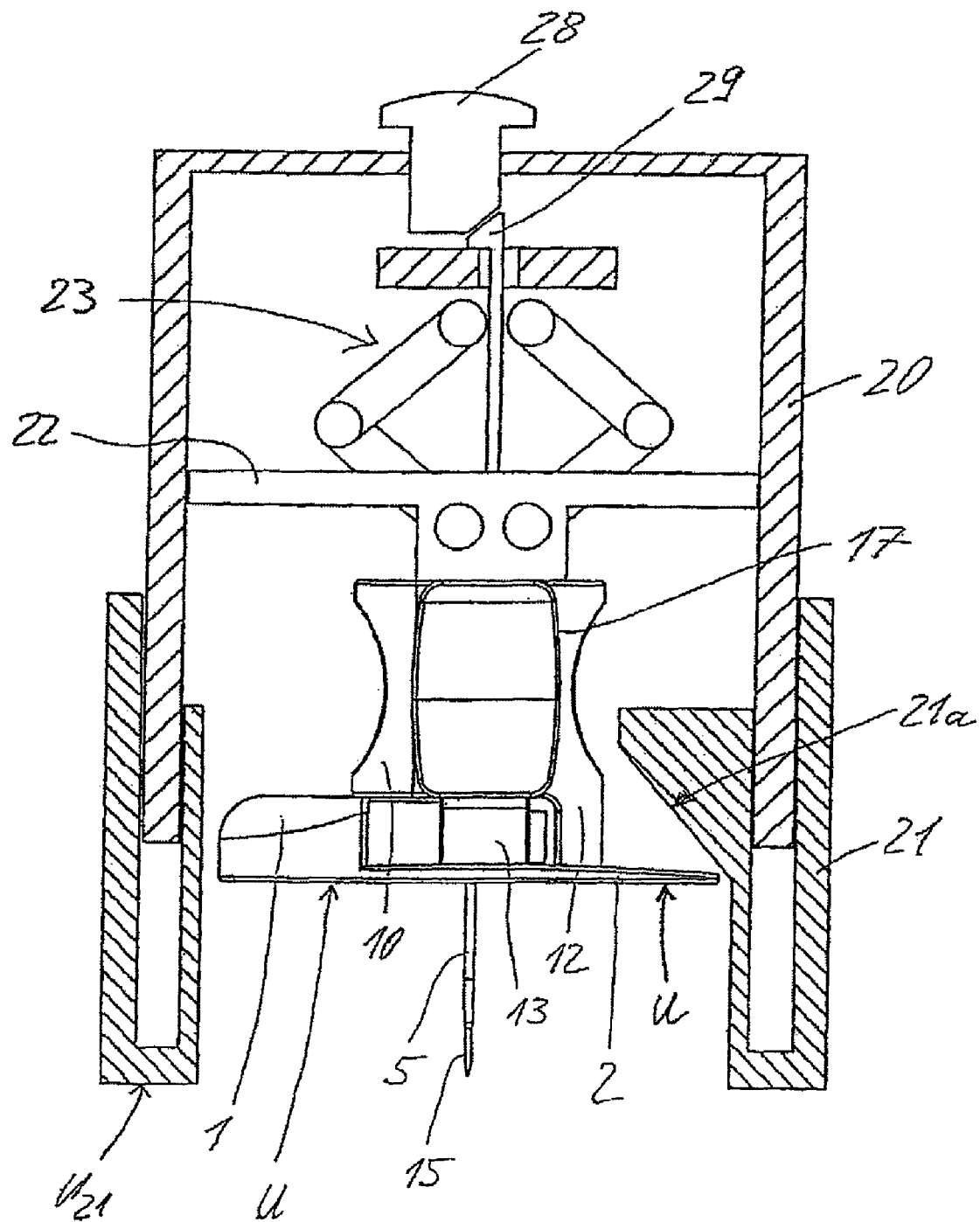
FIG. 11 shows the system of FIG. 10 after actuation.

FIG. 11 shows the system of inserter and insertion head in its activated state. The inserter housing 20 and the actuation member 21 assume the extended position relative to each other. In the extended state, the walls of the inserter housing 20 and of the actuation member 21 surround the activated insertion head to a point beyond the free end of the insertion device 5 and of the puncture device 15, i.e. the tip of the puncture device 15 is set back a short distance behind the underside U21 of the inserter.

In the extended position, the inserter housing 20 and the actuation member 21 are blocked relative to each other. Relative movements in or counter to the thrust direction V are not possible in the blocked state. When the extended position is reached, the inserter housing 20 and the actuation member 21 block automatically with each other.

For placement of the insertion head, the user places the inserter onto the skin surface. With the inserter in place, the user presses on the trigger 28. The trigger 28 acts on the blocking member 29 via a curved joint, in the illustrative embodiment a simple pair of bevels. Under the effect of the trigger 28, the blocking member 29 moves out of the blocking engagement with the inserter housing 20, such that the thrust element 22 can move in the thrust direction V under the effect of the force generator 23. The force generator 23 accelerates the thrust element 22 abruptly. The thrust element 22 acts on the insertion head like a hammer. In the first part of the thrust movement, the retainer spring springs out of the retention engagement with the retaining structure 17 of the insertion head, i.e. the retention engagement is cancelled. The acceleration of the thrust element 22 in the thrust direction V is such that the pure pressure contact between the thrust element 22 and the insertion head is safely maintained until the underside U of the insertion head is at the same level as the underside U21 of the inserter and thus placed on the tissue surface. Before this, the puncture device 15 already pierces the skin surface, penetrates into the tissue, and carries the insertion device 5 with it.

After the insertion head is placed on the skin surface and the inserter is removed, the user takes hold of the grip and pulls it, counter to the direction of insertion, away from the base. In doing so, the puncture device 15 is pulled out of the insertion device 5 and from the base, and, acted on by a spring, then pivots automatically into a protected position in the grip, if appropriate after the two grip components 10, 12 have first of all been pressed together again and then released.

In an advantageous modification of the inserter that also permits automated withdrawal of the puncture device 15, the retention engagement between the retainer device of the inserter and the retaining structure 17 of the insertion head is maintained and, unlike the illustrative embodiment described above, is not cancelled by the acceleration of the thrust element 22. In such a modification, the retainer device can in particular be connected fixedly to the thrust element 22 such that it participates in the latter's ejection movement in the thrust direction V. To cancel the retention engagement, the inserter can be equipped with a stripper which, after the inserter has been removed from the tissue, automatically releases the insertion head from the retention engagement when the inserter housing 20 and actuation member 21 are pushed together, if appropriate after the two grip components 10, 12 have first of all been pressed together again, either automatically or by an additional maneuver, and thereafter released. Alternatively, such a stripper can also be provided completely independently of the actuation member 21 and can be actuated separately to cancel the retention engagement.

Figure 12:
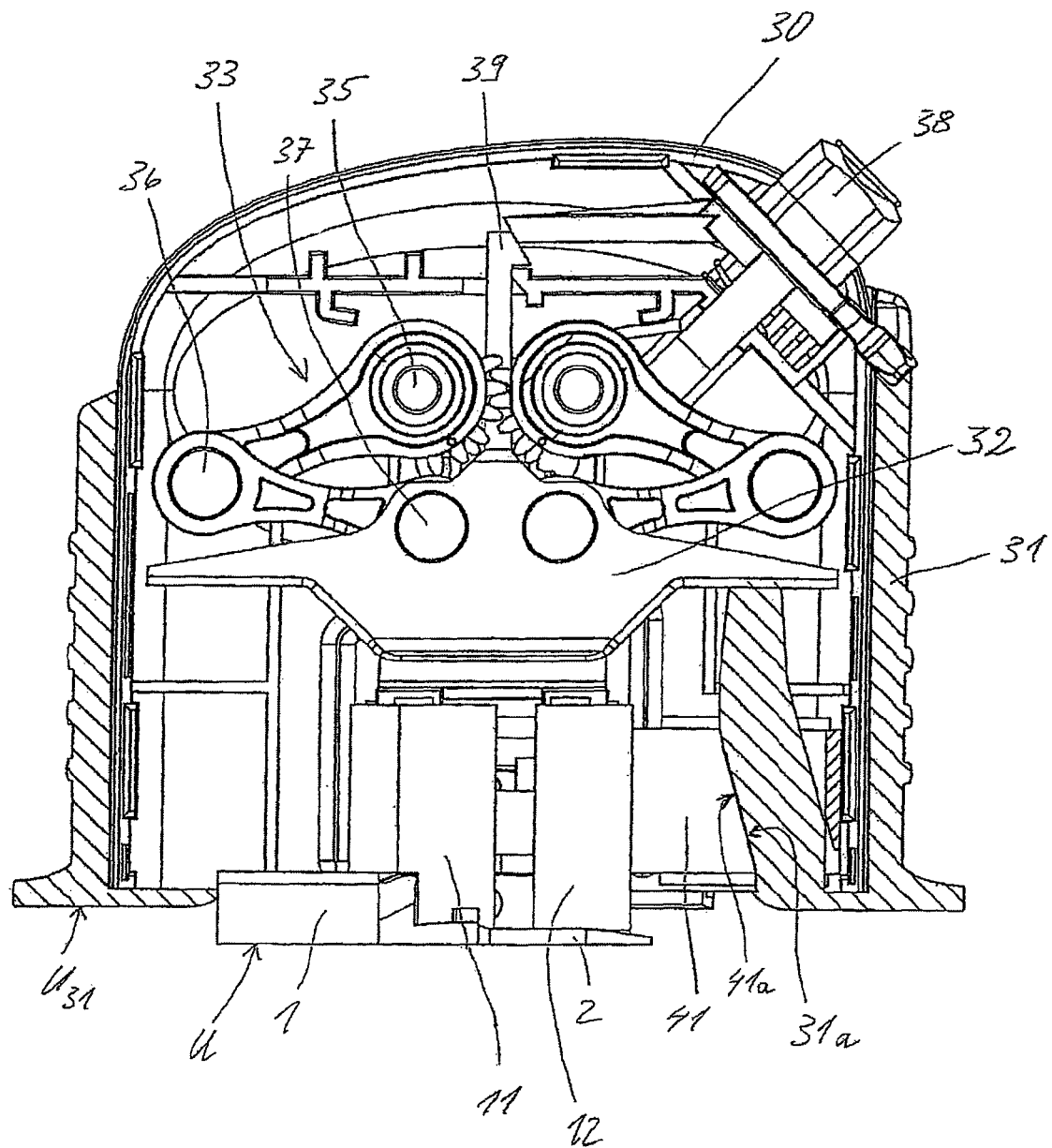
FIG. 12 shows a system composed of an insertion head and of an inserter according to a second illustrative embodiment of the present invention, prior to actuation of the insertion head.
Figure 13:
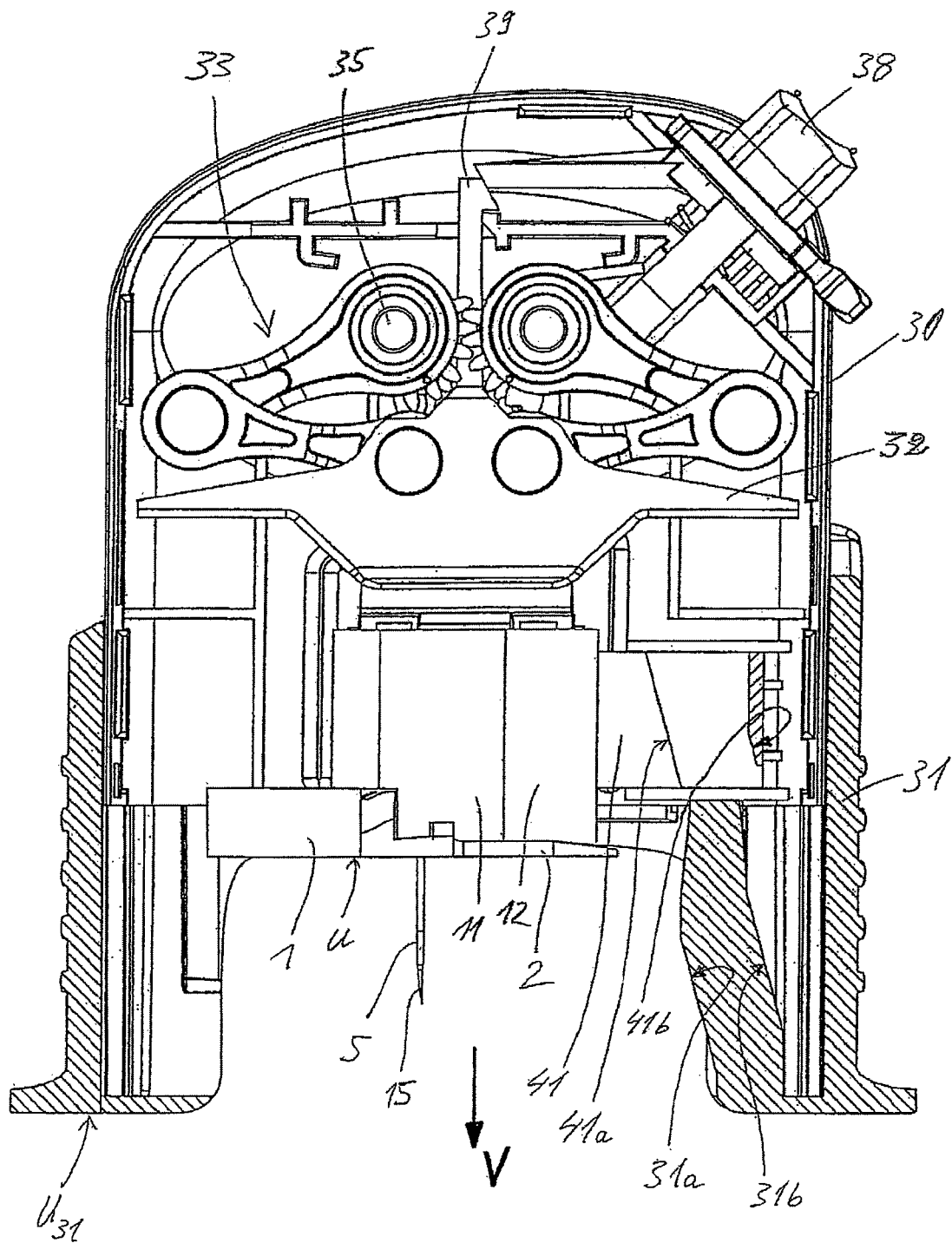
FIG. 13 shows the system of FIG. 12 after actuation.
Figure 14:
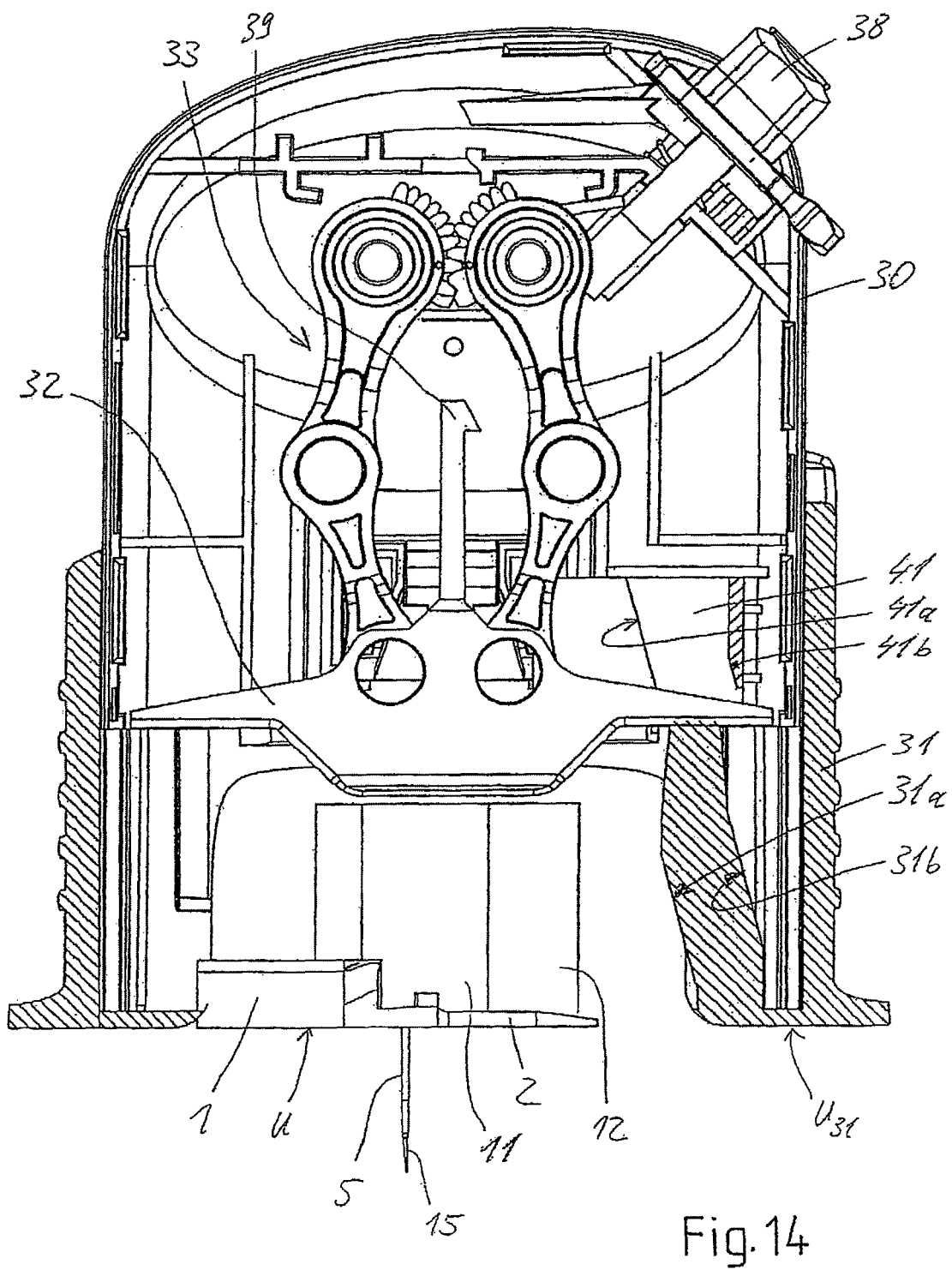
FIG. 14 shows the system of FIG. 12, after the insertion head has been placed on a tissue surface.

FIGS. 12 to 14 show a second illustrative embodiment of a system consisting of an insertion head according to the present invention and an inserter. The insertion head can be the same as in the first illustrative embodiment. The only modification is in the inserter. Those components of the inserter in the second illustrative embodiment which are comparable in function to the components of the inserter in the first illustrative embodiment are each indicated by the references numbers in the first illustrative embodiment plus ten. Thus, particularly as regards the inserter housing 30 and the actuation member 31, their shape and connection and relative mobility are as set out in the statements concerning the first illustrative embodiment. The same also applies in principle in respect of the thrust element 32, the retainer device, the force generator 33, the ejector 38 and the blocking member 39. Unless differences are pointed out below or are evident from the figures, the statements made concerning the first illustrative embodiment apply equally to the second illustrative embodiment.

The inserter of the second illustrative embodiment differs from the inserter of the first illustrative embodiment in respect of the joint via which the actuation member 31 acts on the insertion head to activate the latter by the upward pulling movement of the inserter housing 30 relative to the actuation member 31. In the second illustrative embodiment, the inserter itself forms the joint, namely with two joint elements 31a and 41a, of which one is formed by the actuation member 31, and the other by an effector member 41. The effector member 41 is mounted such that it can move transverse to the thrust direction V, in the illustrative embodiment at right angles to the thrust direction V, back and forth from the insertion housing 30. The joint 31a, 41a is again a curved joint. The guide curve 31a corresponds to the guide curve 21a of the first illustrative embodiment. The effector member 41 forms the engagement element 41a which, upon extension of the inserter, slides along the guide curve 31a and, because of the inclined course of the guide curve 31a, causes a transverse movement of the effector member 41 in the direction towards the central longitudinal axis of the inserter when the latter is pulled upwards. In the joint 31a, 41a, the movement counter to the thrust direction V, which movement is executed by the inserter housing 30 when pulled up relative to the actuation member 31, is thus converted into the transverse movement of the effector member 41. The joint element or engagement element 41a of the latter is itself formed in the manner of a guide curve, but is designated here as an engagement element. Alternatively, the engagement element 41a could also be formed, for example, as a simple cam or knob. Similarly, the engagement element 41a could also be designated as a guide curve and, in another modification, the joint element 31a could be formed as a protruding cam or knob.

The interface via which the inserter activates the insertion head is once again formed as a pure pressure contact and is present between the effector member 41 and the receiving member and movable grip component 12 of the insertion head. This pure, one could almost say loose, pressure contact simplifies handling, since no special hinge connection has to be produced for the activation; all that is needed is the reception of the insertion head in combination with the activation of the actuation member 31, which in the illustrative embodiments is effected by the upward pulling movement. The pressure contact, i.e. the pressure force exerted by the effector member 41, acts on the movable grip component 12 parallel to the direction of its mobility relative to the base. By interposition of the effector member 41 and shifting of the joint 31a, 41a entirely to the inserter, no force is exerted on the grip component 12 in the second illustrative embodiment transverse to the direction of mobility of the grip component 12.

FIG. 13 shows the system with the insertion head activated. In the course of the upward pulling movement of the inserter housing 30, which is also understood as activation of the actuation member 31, the insertion device 5 and the puncture device 15 have been pivoted into the insertion position, such that their common longitudinal axis points in the thrust direction V. In the same way as has been described for the insertion head, the movable grip component 12 has released the connection between the grip and the base. However, the frictional fit between the insertion device 5 and the puncture device 15 holds the base, as in the first illustrative embodiment, on the grip located in the retention engagement.

Actuating the trigger 38 releases the blocking engagement in which the blocking member 39 is still connected to the inserter housing 30 or to a structure securely fixed thereto, and the force generator 33 accelerates the thrust element 32 in the thrust direction V. The acceleration once again takes place abruptly, such that the drive device of the second illustrative embodiment acts also in the manner of a hammer. The drive force is generated by two spiral springs, one of which in each case acts on one of the two pairs of branches. The branches 24 secured in the positionally fixed pivot bearing 35 are coupled to one another by a toothed engagement, which ensures a synchronous outward movement of the two pairs of branches.

To be able to make the inserter ready for reuse after placement of the insertion head, the effector member 41 has to be moved back from the end position shown in FIG. 13 to the end position shown in FIG. 12. For this recovery movement, the actuation member 31 and the effector member 41 form another joint 31b, 41b, which in the illustrative embodiment is once again a curved joint. For said other joint, the actuation member 31 forms the guide curve 31b, and the effector member 41 forms the engagement element 41b. The guide curve 31b extends at least substantially parallel to the guide curve 31a. The guide curves 31a and 31b are formed on the inner sleeve part of the actuation member 31, the guide curve 31a on the inside face and the guide curve 31b on the outside face of the inner sleeve part. They lie opposite each other at approximately the same height relative to the thrust direction V. The engagement element 41b also lies opposite the engagement element 41a with a slight spacing, such that the inner sleeve part of the actuation member 31 can move in and out between the two engagement elements 41a and 41b.

FIG. 14 shows the system of the second illustrative embodiment with the insertion head in place. The inserter is removed from the insertion head. The user then pulls the grip away from the base, and the puncture device is automatically pivoted back into a protected position in the grip, if appropriate after the two grip components 10, 12 have been pushed together again and then released, and the user attaches the insertion head to a catheter of an infusion pump. In a modification which has already been mentioned also with respect to the first illustrative embodiment, and in which the retainer device is connected in a fixed position to the thrust element 32 and can accordingly still hold the grip, the inserter is removed from the base together with the grip still held by it. The retention engagement is then released preferably by an additional stripper, if appropriate after the two grip components 10, 12 have first of all been pushed together again, either automatically or by an additional maneuver, and then released, and the grip is discarded with the puncture device 15.

To prepare the inserter for use with another insertion head, the user slides the inserter housing 30 and the actuation member 31 together again into the retracted position, as is shown in FIG. 12 with the insertion head fitted. During the inward movement, the inner sleeve part of the actuation member 31 travels between the engagement elements 41a and 41b of the effector member 41. This inward movement produces the other joint connection between the guide curve 31b and the engagement element 41b. During the inward movement, therefore, the effector member 41 of the joint (formed by 31b, 41b) is moved back again into the end position shown in FIG. 12, i.e. moved transversely outwardly, e.g. radially, with respect to the central longitudinal axis.

The thrust element 32, driven out in the thrust direction V under the effect of the spring device 33, lies opposite an end face of the inner sleeve part directed away from the underside U31 of the actuation member 31. The advance movement of the thrust element 32 is stopped by abutment against this end face. The actuation member 31 is geometrically dimensioned such that, in the extended position of the telescope (members 30, 31), it stops the thrust element 32 exactly when the underside U of the insertion head has reached the level of the underside U31 and therefore makes exact contact with the skin surface with the inserter in place. During the inward movement of the inserter housing 30 relative to the actuation member 31, or of the actuation member 31 relative to the inserter housing 30, the abutment contact means that the thrust element 32 is pressed by the actuation member 31 deeper into the inserter housing 30 counter to the force of the force generator 33, until the blocking member 39 is once again in blocking engagement, in which it is shown for example in FIGS. 13 and 14.

Figure 15:
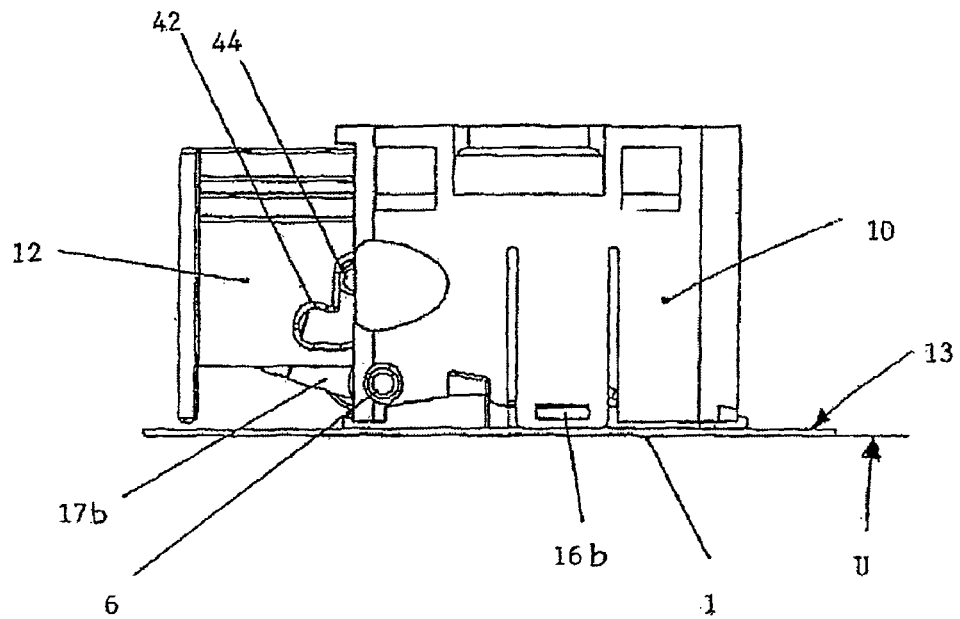
FIG. 15 is a side view of an insertion head, with the insertion device located in the protected position.

FIG. 15 shows another embodiment of the insertion head according to the present invention. The insertion head comprises a second grip component 12 which can be pushed into a first grip component 10 counter to a spring force and then, as in the insertion head according to FIGS. 5 to 9, is locked reversibly onto the latter via a so-called "ballpoint pen mechanism" in such a way that, by pushing the two grip components 10, 12 together again, the locking can be released and the grip components 10, 12 can be moved apart again into the original position by the spring force. By pushing the second grip component 12 into the first grip component 10, a cannula housing 17b is pivoted about a hinge 6. The cannula housing 17b still carries the insertion device 5 and the puncture device 15 in the protected position. During the actuation of the second grip component 12, the sliding block 44 in the guide slot 42 is driven substantially downwardly in the direction of the hinge element 6, which leads to a rotational or pivoting movement of the insertion device and puncture needle. As soon as the sliding block or stud 44 has arrived in the curve area of the guide slot 42, the pivoting movement from the protected position to the insertion position is completed. The first grip component 10 is also equipped with a connection device 16b which is in engagement with a corresponding section 49 (see FIG. 17) on the base to connect the base reversibly to the grip.

Of course, the sliding block can also have another position. Thus, the sliding block 44 could also be arranged further down and, upon pivoting of the components, would then migrate substantially upward. Various configurations of the guide slot and sliding block are possible.

Figure 16:
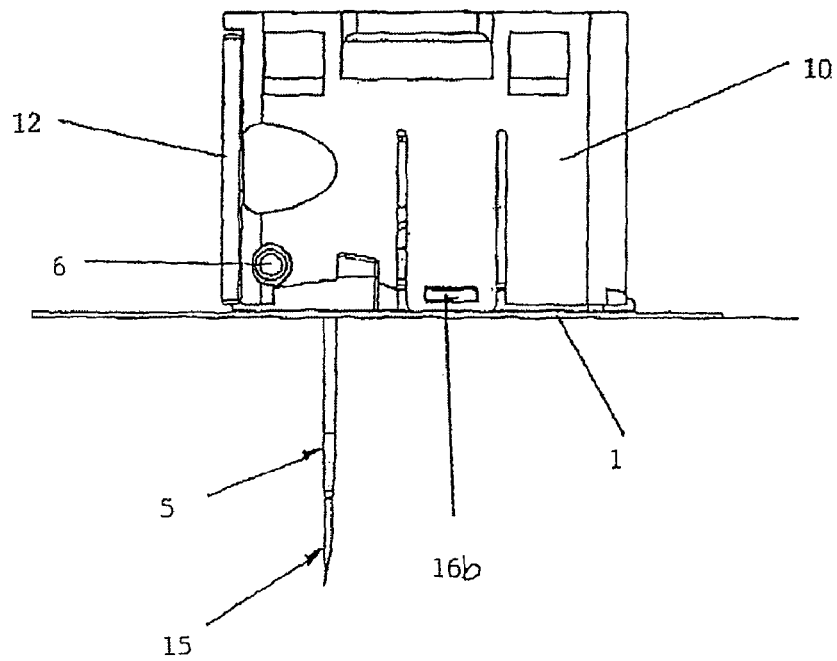
FIG. 16 shows the insertion head according to FIG. 15, with the insertion device located in the insertion position.

According to FIG. 16, the second grip component 12 is pushed into the first grip component 10 and locked reversibly to it, and the insertion movement of the second grip component 12 into the first grip component 10 leads to a pivoting of the insertion device 5, together with the puncture device 15, from the seat 14 (see FIG. 18) into the insertion position.

From FIG. 17, which shows the grip and the puncture device 15 held in it separated from the applied cannula housing 17b with base 1 and cannula 5, it will be seen how the grip, consisting of grip components 12 and 10, can be uncoupled from the base 1. The base 1 comprises a recess 49 with which a connection device 16b of the grip engages in the protected position (FIG. 15). When the two grip components 10, 12 are pushed together, this engagement is cancelled, such that the grip can be removed from the base 1.

FIG. 18 shows the grip according to FIG. 17, but here the two grip components 10, 12 have been pushed into one another again in the sliding direction and the lock between these two components 10, 12 has been cancelled and they have been pushed apart again into the original position under the force of an internal spring, such that the sliding block or stud 44 in the guide slot 42 has been guided substantially upwards, as a result of which the needle holder, with the puncture device 15 secured thereon, has been pivoted again, specifically into the original protected position in the seat 14 or to a catch position near the latter.

FIG. 19 shows another preferred embodiment of the insertion head according to the present invention in a situation prior to application or during storage. The insertion device 5, with the puncture device 15 partially received therein, is located in the protected position in the seat 14. A protective film is applied to the underside U of the tab or plaster 13 to keep the adhesive areas of the plaster 13 active. According to FIG. 19, a septum 58 is also provided, which is intended to permit insertion and withdrawal of the puncture device 15, and thereafter to guarantee a seal for the insertion device 5. Correspondingly, a septum 56 is also provided for the section adjoining the puncture device 15 at right angles, which septum 56 is intended to permit a tight connection to a delivery line or a convector (see FIG. 27).

On a needle holder 17a, which is arranged on the cannula housing 17b and which holds the puncture device 15, the side directed away from the base 1 is provided with a securing structure 46, which can be seen from the detail shown in FIG. 19a. In the state illustrated here, an engagement element 48 is in engagement with the securing structure 46 and offers a resistance that counters inadvertent insertion of the second grip component 12 into the first grip component 10. The person using the inventive insertion head according to this embodiment must initially apply considerable force to overcome the engagement between the engagement element 48 and the securing structure 46 and thus bring about the pivoting movement of the insertion device 5 and puncture device 15 from the protected position in the seat 14, as shown in FIG. 19, to the application position, as shown in FIG. 20. At the same time, for the pivoting movement, it is additionally necessary to overcome the spring force of two pretensioned rubber bands 65 acting as tension springs, which are increasingly pretensioned as the pivoting movement increases.

It is also possible to design the securing structure 46 with locking devices which correspond to the elements 52, 54 and which, for example, can be provided on the first and second grip components 10, 12 and can be unlocked by one of these being pushed into the other.

Figure 21:
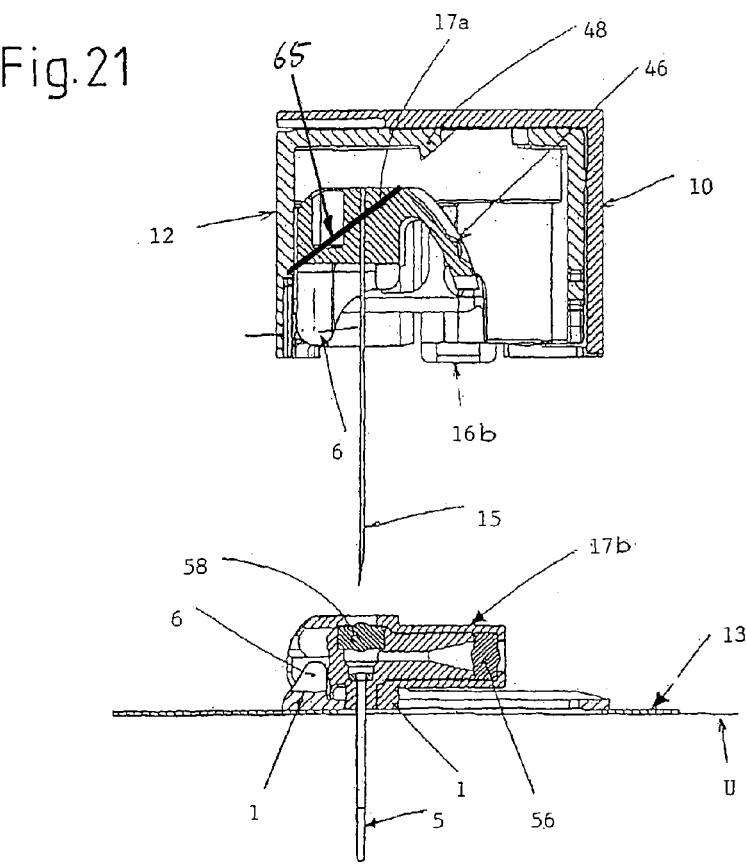
FIG. 21 is a sectional view of the grip and puncture device when separated from the base and the insertion device, which can be placed on the patient.

The insertion device 5 with puncture device 15 introduced into the tissue of a patient in FIG. 20 is shown in the disconnected state in FIG. 21. In other words, the puncture device or puncture needle 15 has been pulled out of the insertion device 5. The septum 58 closes, and the insertion device 5 is ready to introduce a medicament into the body of a patient.

Figure 22:
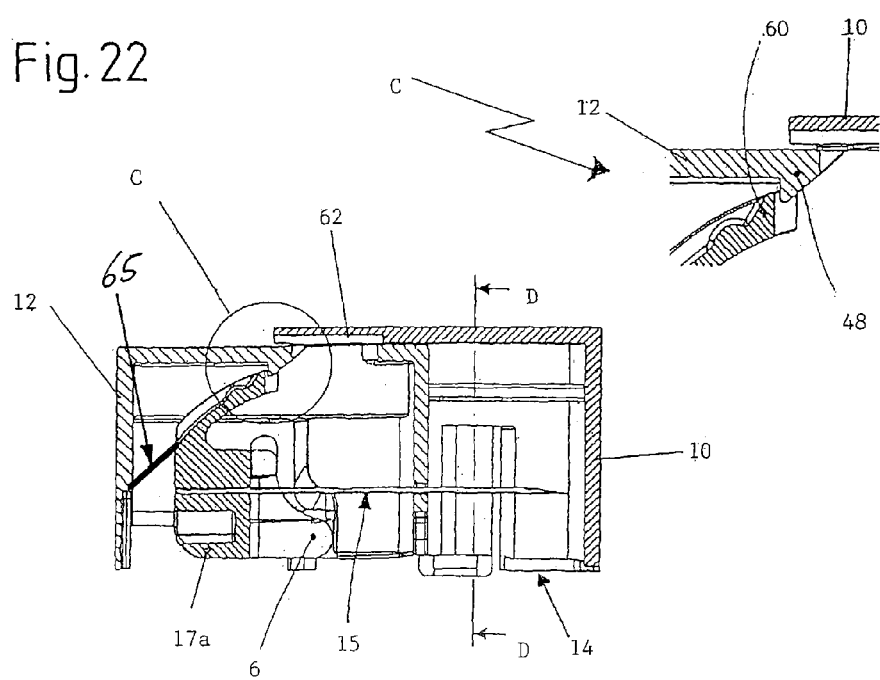
FIG. 22 is a sectional view of the first and second grip components after the second grip component has been pushed out of the first grip component, and beside this includes an enlarged detail C, likewise in sectional view.
Figure 22A:
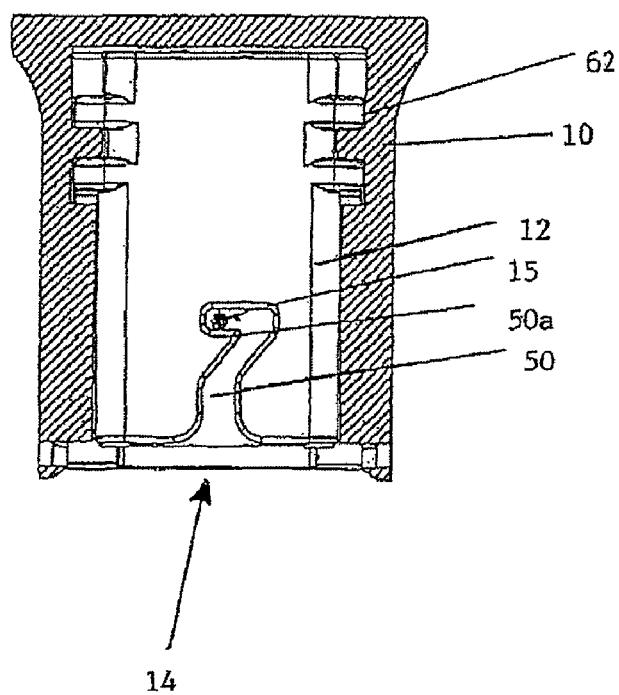
FIG. 22a is a cross section along line D-D of FIG. 22, oriented perpendicular to the cross section in FIG. 22.
Figure 23:
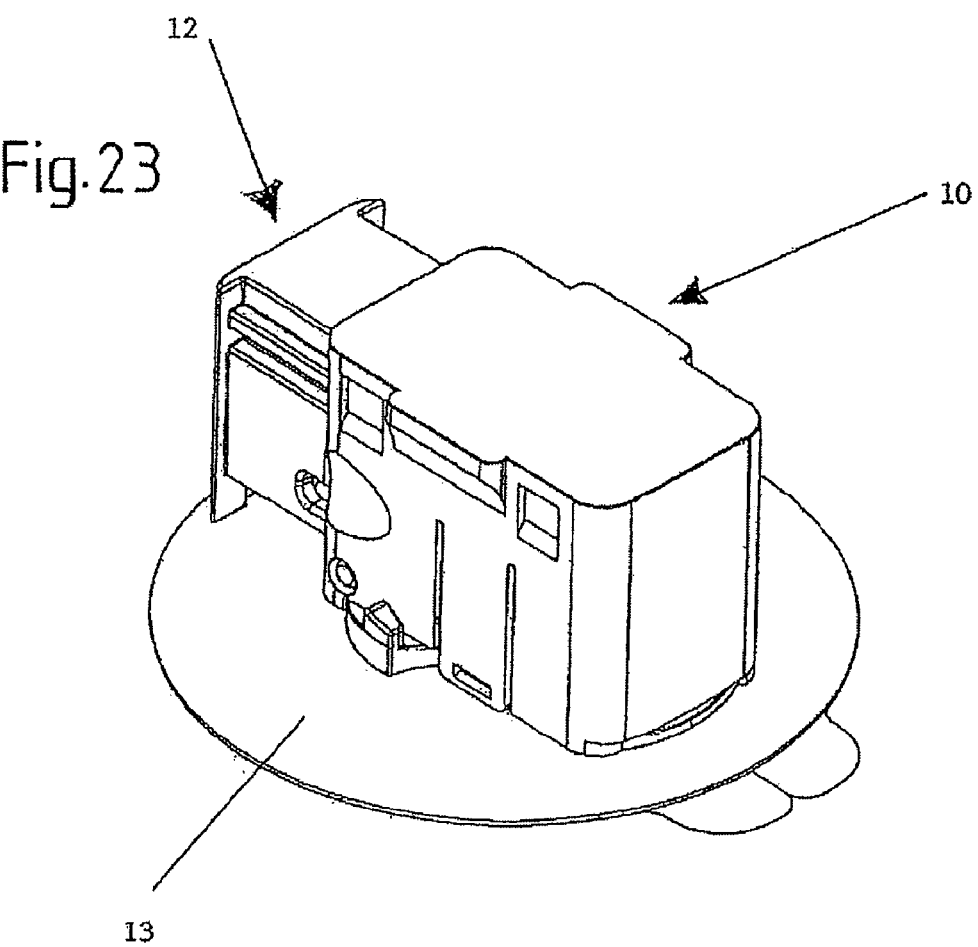
FIG. 23 shows an embodiment of an insertion head according to the present invention in a perspective view, prior to application.
Figure 24:
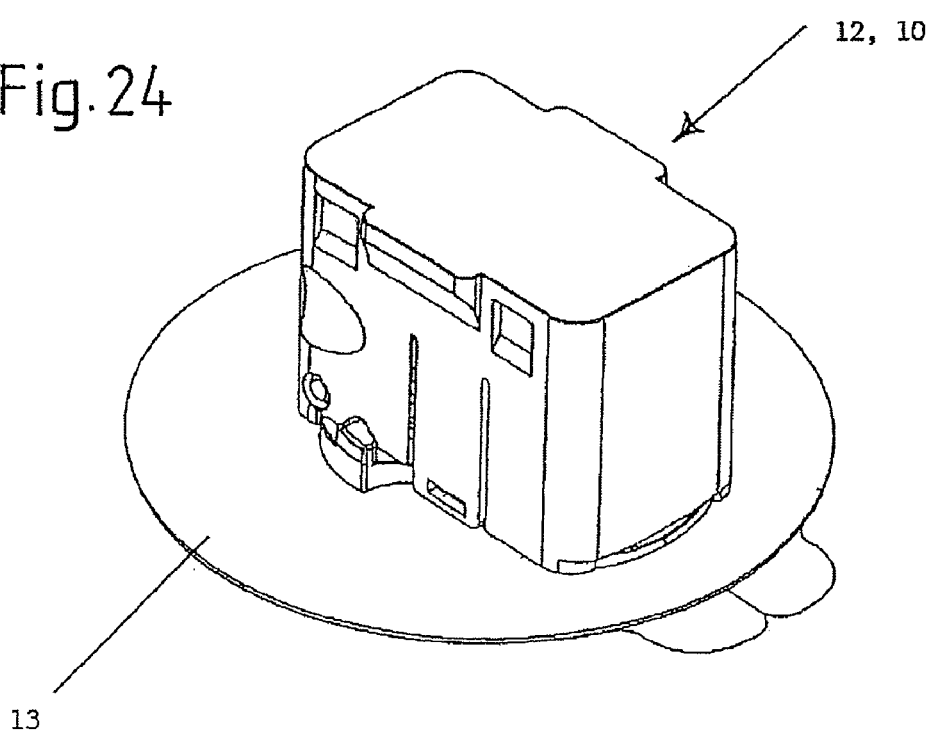
FIG. 24 shows the insertion head of FIG. 23 after application.

After the puncture device has been withdrawn from the septum 58, it is possible, by decreasing the compressive force exerted on the two grip components 10, 12, to effect an automatic restoring movement of the puncture device 15, under the force of the two rubber bands 70, into a protected position. This situation is shown in FIG. 22. Here, the puncture device 15 is moved past the original protected position into a position above the protected position, i.e. above a locking shoulder 60, which is explained below. As can be seen from the enlarged detail C, the puncture device 15 is secured in this position by virtue of the fact that a locking shoulder 60 at the end of the needle holder 17a comes into engagement with the engagement element 48. In this position, it is now no longer possible for the contaminated puncture device 15 to be deflected again out of the grip, because a blocking action is provided by the engagement element 48 in conjunction with the locking shoulder 60. The puncture device 15 is held in a blocked position behind the locking shoulder. A cross section D-D from FIG. 22 is shown in FIG. 22a, to illustrate a securing slot 50 which serves to transfer the used and contaminated puncture device 15 into a secure slot area behind a securing shoulder 50a. By contrast, the unused and sterile puncture device can be held, prior to use, in another position in front of the securing shoulder 50a.

The cross-sectional view according to FIG. 22a also shows guides 62, which allow the second grip component to be guided inside the first grip component 10. When the puncture device 15 is pivoted back into an inactive position in the seat 14, it will move, deforming flexibly, through the securing slot 50, thereafter to return to shape in the upper area of the securing slot 50 behind the securing shoulder 50a and to spring back into a position shown in FIG. 22a, then to catch in the depicted position and be blocked there.

FIGS. 23 to 28 show various stages in the application of an insertion head according to the present invention with a similar function to the one discussed above. Here, however, the two grip components 10, 12, when first pushed together, which serves to pivot the insertion device 5 and puncture device 15 out from the protected position into the insertion position, are locked onto each other via a so-called "ballpoint pen mechanism", in such a way that this locking can be cancelled by pushing the two grip components 10, 12 together again. The way in which such a "ballpoint pen mechanism" can be obtained has already been explained with reference to FIGS. 5 to 9 and is also familiar to persons skilled in the art, such that it does not have to be discussed in detail here. According to FIG. 23, the second grip component 12 is shown in a position in which it is protruding from the first grip component 10, in which position the insertion device 5 and puncture needle 15 are in their protected position. In the view according to FIG. 24, the second grip component 12 has been moved into the first grip component 10 and locked onto the latter, such that, as can be seen from FIG. 25, the insertion device and puncture device can be introduced into the body of a patient.

Figure 25:
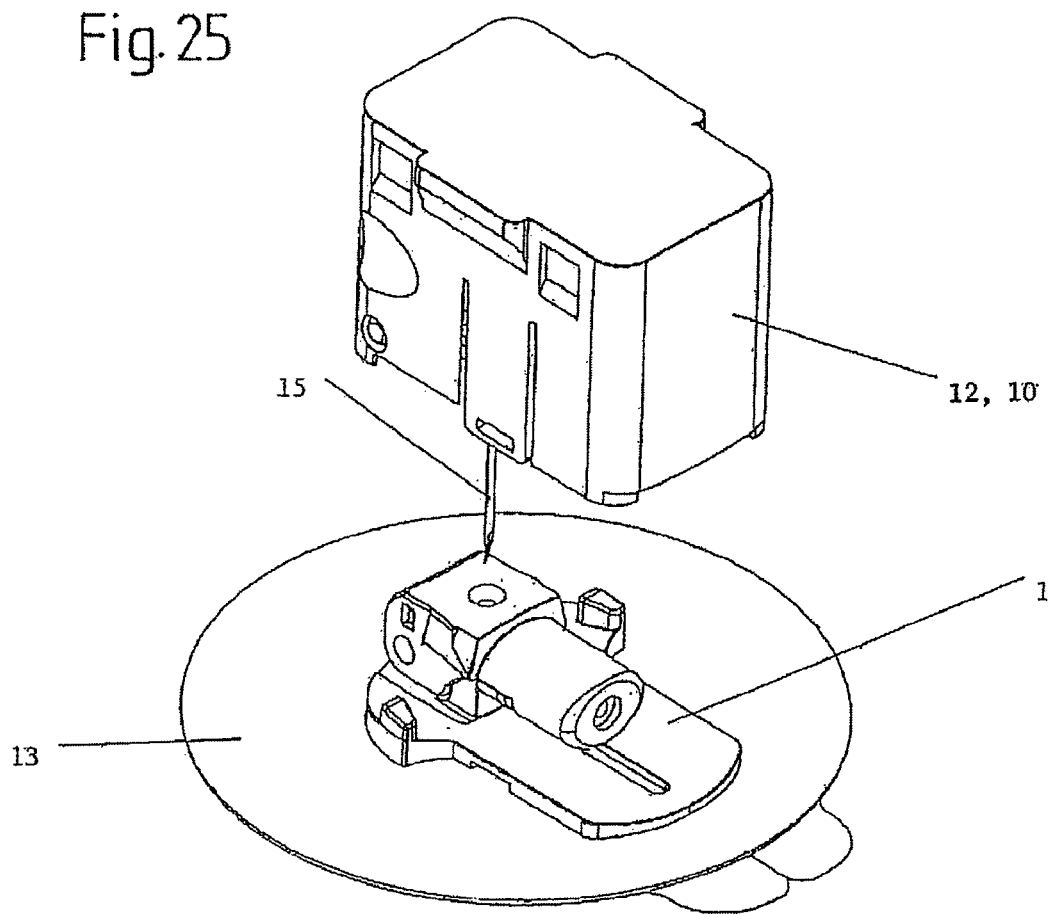
FIG. 25 shows the insertion head according to FIGS. 23 and 24 after removal of the first and second grip components and puncture needle.
Figure 26:
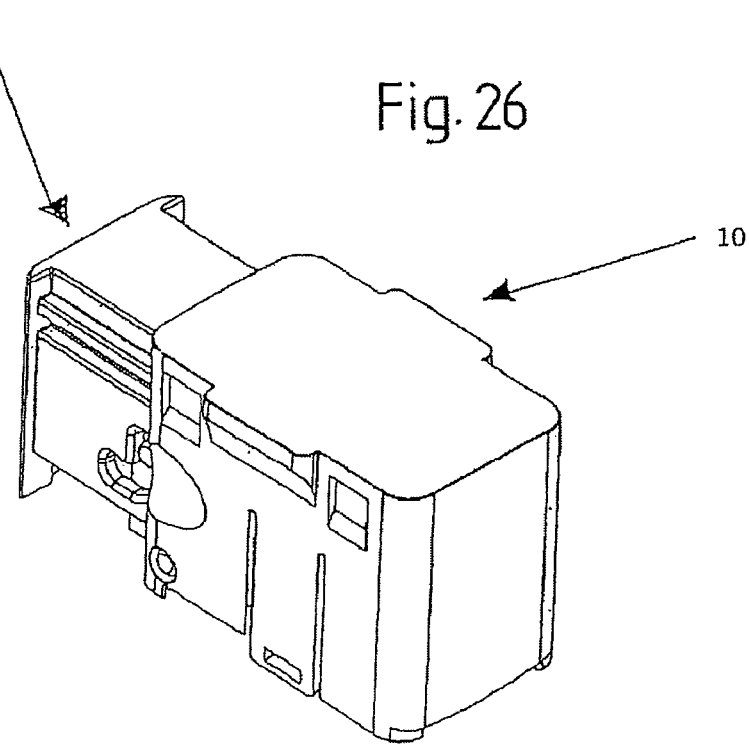
FIG. 26 shows the first and second grip components in a perspective view, after the second grip component has been pulled out of the first grip component.

FIG. 25 now shows the state after the insertion device and the puncture device 15 have been introduced into the body of a patient and the puncture device 15 with the grip 10, 12 has been separated from the base 1 with the insertion device.

By pushing the two grip components 10, 12 into one another again in the situation shown in FIG. 25, the locking of the two grip parts 10, 12 is cancelled, such that the second grip component 12 is pressed by the force of the inner spring back out of the first component 10, with the puncture device 15 being transferred to a protected position inside the boundaries formed by the grip components 10, 12.

Figure 27:
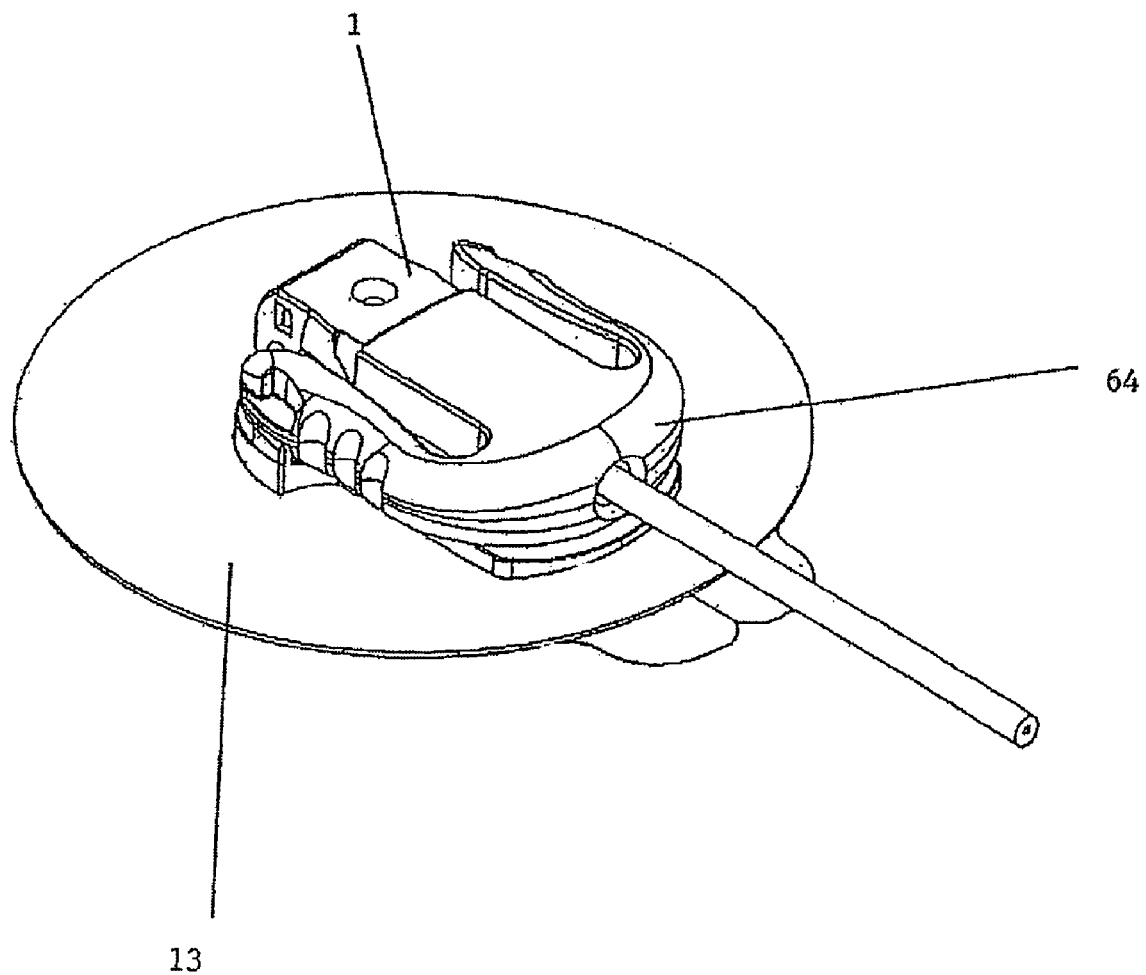
FIG. 27 shows the base of the insertion head according to FIGS. 23 to 26, after attachment of a connector piece for delivering a medicament.

As is shown in FIG. 27, a connector 64 with a delivery line can now be attached to the base to deliver a medicament, for example insulin.

Figure 28:
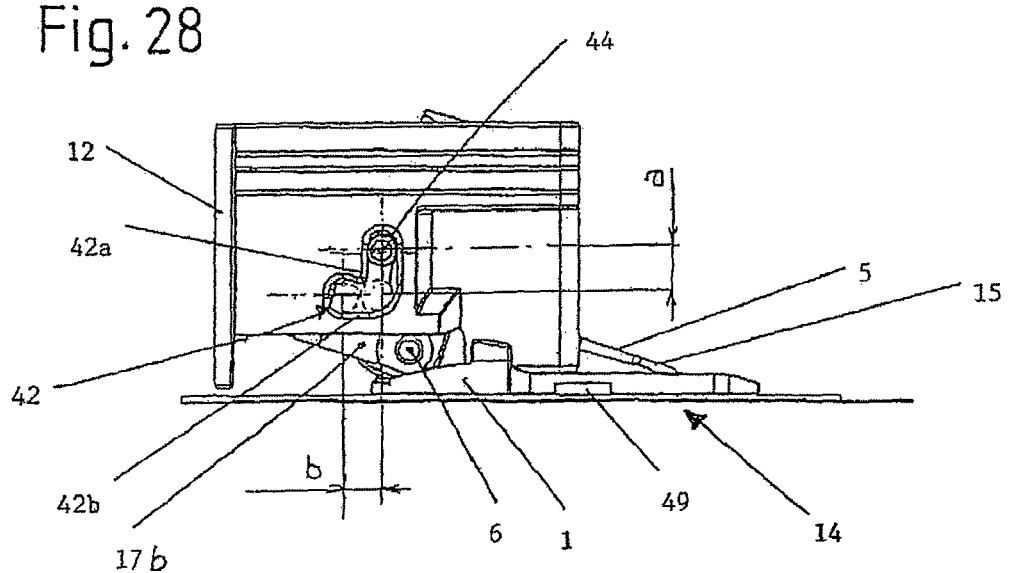
FIG. 28 shows an insertion head with the insertion device and puncture needle located in the protected position, depicted without the first grip component.

FIG. 28 shows that the guide slot 42 has a first section 42a of length a. This distance a allows the cannula housing 17b, and with it the insertion device 5 and puncture device 15, to pivot to the right in the present case, by actuation of the second grip component 12, such that the sliding block 44 moves substantially downwards in the direction of the hinge element 6, while the insertion device 5 is transferred from the protected position to the application position or insertion position. A second section 42b of the guide slot 42 is available which, via the second distance b, provides a clearance that allows unlocking to be performed, so as to guide the connection device 16b out of the engagement recess 49.

Figure 29:
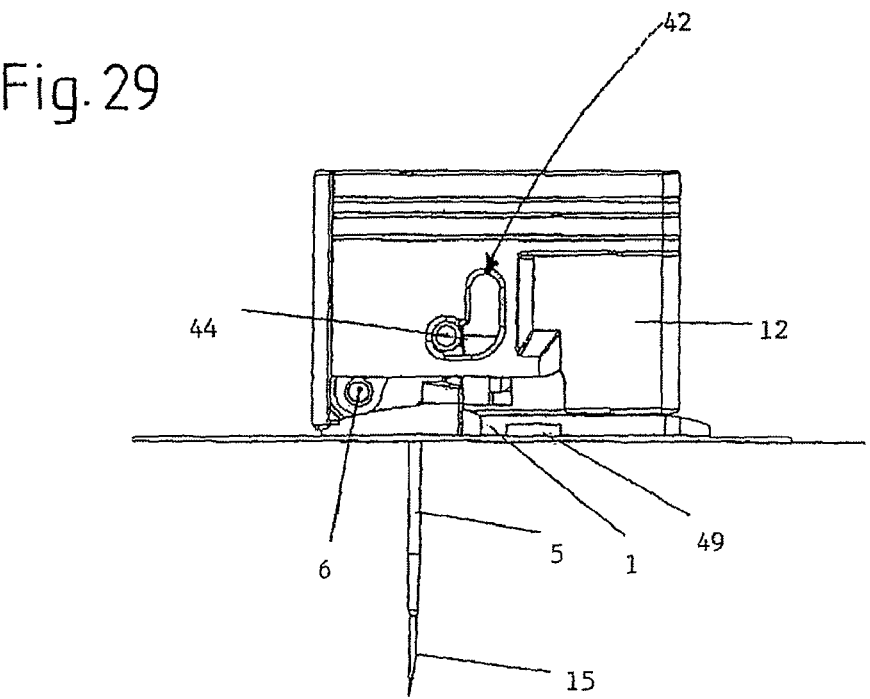
FIG. 29 shows the insertion head of FIG. 28, with the insertion device and puncture needle in the application position.

According to FIG. 29, in which the sliding block 44 has arrived at the other end of the guide slot 42 relative to the view according to FIG. 28, not only are the insertion device 5 and puncture device 15 in their application position, the grip is also already unlocked relative to the base 1 and can be released, with the puncture device 15 being pulled out of the insertion device 5.

Figure 30:
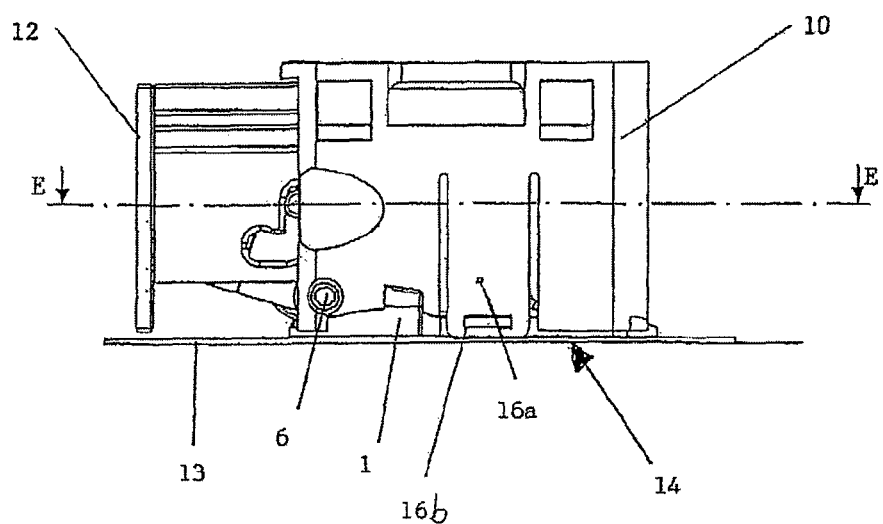
FIG. 30 is a side view of an insertion head with the insertion device located in the protected position.
Figure 31:
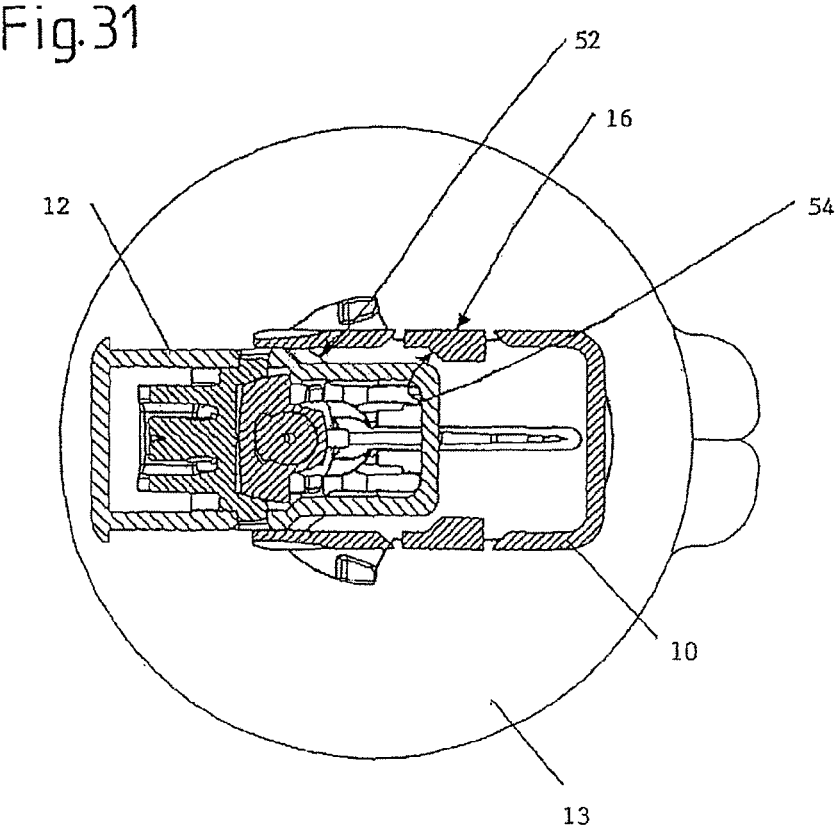
FIG. 31 is a cross section along line E-E of FIG. 30 in a plan view.

In the embodiment according to FIG. 30, an unlocking mechanism is also shown, which is particularly seen in the cross section E-E depicted in FIG. 31. As can be seen, the second grip component 12 has a control ramp 52 which, after insertion of the second grip component 12 into the first grip component 10, runs up against a deflector ramp 54, in this way to convey the connection element 16 out of its engagement with the engagement recess 49 on the base 1. While the movement for pivoting the insertion device 5 and puncture device 15 corresponds to the distance 42a with the length a, the movement for guiding the control ramp 52 to the deflector ramp 54 corresponds to the section 42b of the guide slot 42 according to FIG. 28.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion head for medical use, comprising a housing formed by two housing parts movable relative to each other, a base separable from the housing, a puncture needle and a flexible cannula supported by the puncture needle, the puncture needle and cannula pivotal between a protected position inside the housing and an insertion position outside the housing in which the puncture needle and cannula can be inserted into the body of a patient, the puncture needle and cannula pivoting in response to the relative movement of the two housing parts, and a cannula housing securely connected to the cannula and pivoting with the cannula, and wherein after insertion the puncture needle is removed from the cannula, cannula housing, and base by moving the housing and puncture needle away from the body counter to the direction of insertion, the puncture needle being automatically pivoted into the protected position after removal from the cannula, and wherein the base, and cannula housing remain on the body of the patient and the cannula remains in the body of the patient.

2. An insertion head for medical or pharmaceutical applications, comprising:
   a) a housing comprising a first housing part and a second housing part movable relative to each other;
   b) a base separable from the housing;
   c) a flexible insertion device stabilized by a puncture device, the insertion device and the puncture device each having a free end and mounted so as to be jointly movable relative to the housing, the end of the insertion device opposite the free end being securely connected to an insertion device housing,
   d) the insertion device and the puncture device being pivotal relative to the housing from a protected position, in which the free ends are inside the housing, to an insertion position in which the free ends are outside the housing, the insertion device housing pivoting with the insertion device; and
   e) a coupling converting the relative movement of the two housing parts into a pivotal movement of the insertion device and the puncture device from the protected position to the insertion position, wherein when the puncture device is in the insertion position, the puncture device is connected to the housing and releasable from the insertion device, and wherein after insertion of the insertion device and the puncture device, the puncture device is removed from the insertion device, the insertion device housing, and the base by moving the housing in a direction counter to the direction of insertion, the puncture device moving automatically to the protected position after removal from the insertion device, the base and insertion device housing remaining on a patient and the insertion device remaining in the patient.

3. The insertion head according to claim 2, further comprising restoring means for pivoting the puncture device automatically to the protected position.

4. An insertion head for medical or pharmaceutical applications, comprising:
   a) a housing comprising a first housing part and a second housing part, the first and second housing parts being movable relative to each other;
   b) a base separable from the housing, the base having an underside;
   c) a flexible insertion device, which is stabilized by a puncture device, the insertion device and the puncture device each having a free end and being mounted so as to be jointly pivotal relative to the housing, the end of the insertion device opposite the free end being securely connected to an insertion device housing,
   d) the insertion device and the puncture device being pivotal relative to the housing from a protected position, in which the free ends of the insertion device and of the puncture device are arranged inside the housing and/or the base, to an insertion position, in which the free ends protrude from the housing and/or the base in such a way that they can be inserted into organic tissue, the insertion device housing pivoting with the insertion device, and
   e) a coupling converting the relative movement of the two housing parts into a pivotal movement of the insertion device and the puncture device from the protected position to the insertion position, wherein when the insertion device and the puncture device are in the insertion position and protruding from the base and the underside of the base is placed on the organic tissue, the insertion device and the puncture device are inserted into the organic tissue, wherein when the puncture device is in the insertion position, the puncture device is connected or connectable to the housing and released or releasable from the insertion device, and wherein after insertion of the insertion device and of the puncture device into the organic tissue, the puncture device is removed from the base, the insertion device housing, and the insertion device by moving the puncture device in a direction counter to the direction of insertion, the base and the insertion device housing remaining on the organic tissue and the insertion device remaining in the organic tissue, and further comprising restoring means for pivoting the puncture device automatically to the protected position.

5. The insertion head according to claim 4, wherein when the two housing parts are gripped between two fingers of one hand and, one finger is pressed against one of the housing parts, the second housing part is moved in the direction of the first housing part.

6. The insertion head according to claim 4, wherein the base is connected immovably to the insertion device, such that, upon movement from the protected position to the insertion position, the base is moved relative to the housing.

7. The insertion head according to claim 4, wherein, with the insertion device and puncture device in the protected position, the underside of the base forms at least a part of an outer face of the housing, such that, in the protected position, the free ends are set back behind the underside of the base and, upon movement from the protected position to the insertion position, the insertion device and the puncture device are moved relative to the base such that the free ends protrude beyond the underside of the base in the insertion position.

8. The insertion head according to claim 7, wherein the insertion device is mounted movably in the base.

9. The insertion head according to claim 8, wherein the base and one of a hinge element or a guide element of a sliding guide together form one of a hinge or a sliding guide, and the insertion device protrudes from the hinge element or the guide element.

10. The insertion head according to claim 9, wherein the housing extends upwards from a top face of the base.

11. The insertion head according to claim 4, wherein the two housing parts are pivotable relative to each other and slideable one inside the other to effect the movement of the insertion device and puncture device from the protected position to the insertion position.

12. The insertion head according to claim 11, wherein the two housing parts are linearly displaceable relative to each other to effect the movement of the insertion device and puncture device from the protected position to the insertion position.

13. The insertion head according to claim 12, wherein the two housing parts are displaceable substantially parallel to the underside of the base.

14. The insertion head according to claim 4, wherein the coupling couples the one of the two housing parts to the insertion device by a toothed engagement, and comprises a toothed wheel and a toothed rack.

15. The insertion head according to claim 14, wherein one of the two housing parts is connected to the toothed rack, and the insertion device is connected to the toothed wheel which is in toothed engagement with the toothed rack.

16. The insertion head according to claim 15 wherein the insertion device is pivotable about a rotation axis and is connected in a rotationally fixed manner to a toothed wheel which rotates about the rotation axis and is in toothed engagement.

17. The insertion head according to claim 4, wherein the insertion device or the puncture device is held via a rotation shaft on the base or on a first of the two housing parts, a sliding block is arranged eccentrically with respect to the rotation shaft, a guide slot is operatively engaged with the sliding block such that a movement of the two housing parts relative to each other transfers the sliding block, guided by the guide slot, from a first position, which corresponds to the protected position of the insertion device and puncture device, to a second position, which corresponds to the insertion position of the insertion device and puncture device.

18. The insertion head according to claim 4, wherein the housing is connected releasably to the base and the connection is released during the movement of the two housing parts for moving the insertion device and the puncture device from the protected position to the insertion position, and during a subsequent movement of the two housing parts relative to each other.

19. The insertion head according to claim 18, wherein a first connection element is formed on the base and a second connection element is formed on the housing, the first and second connection elements engage with each other to create the connection, and at least one of the first and second connection elements can be moved out of said engagement counter to an elasticity force.

20. The insertion head according to claim 19, wherein the first connection element and second connection element engage with each other to create the connection, and one of the two housing parts, during its movement, contacts one of the first or second connection elements and moves the one of the first or second connection elements out of said engagement counter to an elasticity force.

21. The insertion head according to claim 20, wherein when one of the two housing parts is pushed into the other of the two housing parts upon completion of the movement of the insertion device and the puncture device from the protected position to the insertion position, a control ramp on the first housing part abuts against a deflector ramp on one of the first or second connection elements, which connects the base reversibly to the housing, and deflects the one of the first or second connection elements from an engagement position such that the housing and the base can be separated.

22. The insertion head according to claim 21, wherein a movement of the two housing parts relative to each other along a first distance of a first portion of a guide slot transfers a sliding block, guided by the guide slot, from a first position, which corresponds to the protected position to a second position, which corresponds to the insertion position of the insertion device, and a connection device is provided that connects the base reversibly to the housing, and to release the housing from the base, one of the two housing parts is moved relative to the base along a second distance perpendicular to the direction of extent of the insertion device located in the insertion position, the guide slot having a second portion corresponding to the second distance.

23. The insertion head according to claim 4, wherein during the movement of the insertion device and puncture device into the insertion position, the puncture device connects itself to the housing.

24. The insertion head according to claim 4, wherein the base forms a seat that receives the insertion device and puncture device in the protected position.

25. The insertion head according to claim 4, wherein the housing forms a seat that receives the insertion device and puncture device in the protected position.

26. The insertion head according to claim 4, further comprising a securing structure which reversibly secures the insertion device and puncture device in the protected position.

27. The insertion head according to claim 26, wherein the insertion device housing is moved along with the insertion device, the insertion device housing comprising the securing structure which lies opposite a wall of one of the housing parts extending parallel to the direction of movement of the two housing parts relative to each other, and an engagement element on an inside face of the wall in reversible engagement with the securing structure in the protected position of the insertion device.

28. The insertion head according to claim 4, wherein, in the one or the other of the two housing parts that receives the insertion device and puncture device in the protected position a securing slot is provided into which the insertion device and puncture device can be locked in the protected position.

29. The insertion head according to claim 4, further comprising a retainer element which, during the automatic reverse movement of the puncture device to a protected position, is moved along with the puncture device, the retainer element having a locking shoulder which, upon the automatic reverse movement in the housing, comes into locking engagement with an engagement element to prevent the puncture device from moving out of the housing again.

* * * * *